United States Patent [19]
Anderson et al.

[11] 4,064,139
[45] Dec. 20, 1977

[54] SUBSTITUTED 9,10-DIHYDROANTHRACEN-9,10-IMINES

[75] Inventors: Paul S. Anderson, Lansdale; Marcia E. Christy, Perkasie; Gerald S. Ponticello, Lansdale, all of Pa.

[73] Assignee: Merck & Co., Inc., Rahway, N.J.

[21] Appl. No.: 736,672

[22] Filed: Oct. 28, 1976

Related U.S. Application Data

[63] Continuation-in-part of Ser. No. 564,011, April 7, 1975, abandoned, which is a continuation-in-part of Ser. No. 470,093, May 15, 1974, abandoned.

[51] Int. Cl.$^2$ ............................................. C07D 487/04
[52] U.S. Cl. .......................... 260/313.1; 260/326.25; 260/326.5 B; 260/326.62; 260/326.9; 424/274
[58] Field of Search ...................... 260/313.1, 326.5 B, 260/326.25, 326.9, 326.62

[56] References Cited

U.S. PATENT DOCUMENTS 3,678,072  7/1972  Klanderman et al. ........ 260/326.5 B
3,726,897  4/1973  Schindler et al. ................. 260/313.1

OTHER PUBLICATIONS

Kricka et al., J. Chem. Soc., Perkins I, pp. 766–771 (1973).
Emmett et al., Tetrahedron 22, 1101, (1966).
Harrison et al., Tetrahedron 24, 4589, (1968).
Wittig et al., Annalen 630, 10 (1960).
Bolhuis et al., J. Chem. Soc. Chem. Comm. 870, (1974).

Primary Examiner—Paul M. Coughlan, Jr.
Assistant Examiner—Jose Tovar
Attorney, Agent, or Firm—Harry E. Westlake, Jr.; William H. Nicholson

[57] ABSTRACT

Substituted 9,10-dihydroanthracen-9,10-imines are disclosed to be minor tranquilizers, anticonvulsnts, muscle relaxants, and to be useful in the treatment of extrapyramidal disorders such as Parkinson's disease; also disclosed are processes for the preparation of such compounds; pharmaceutical compositions comprising such compounds; and methods of treatment comprising administering such compounds and compositions.

55 Claims, No Drawings

SUBSTITUTED 9,10-DIHYDROANTHRACEN-9,10-IMINES

BACKGROUND OF THE INVENTION

This application is a continuation-in-part of copending application Ser. No. 564,011, filed Apr. 7, 1975, now abandoned which is a continuation-in-part of copending application Ser. No. 470,093, filed May 15, 1974, now abandoned.

This invention relates to certain substituted 9,10-dihydroanthracen-9,10-imines and their pharmaceutically acceptable salt, ester, and amide derivatives which are useful as minor tranquilizers, anticonvulsants, muscle relaxants, and in the treatment of extrapyramidal disorders such as Parkinson's disease. For convenience the compounds of this invention will hereinafter be referred to as "anthracenimines".

This invention also relates to processes for the preparation of such anthracenimines, to pharmaceutical compositions comprising such compounds, and to a method of treatment comprising administering such compounds and compositions.

The compounds of the present invention may generically be represented by the following structural formula:

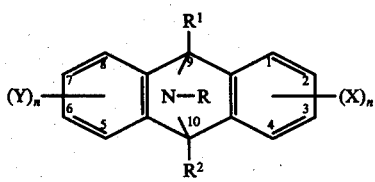

I wherein
- R is hydrogen, acyl, alkyl, aryl, alkoxycarbonyl, aralkyl, alkenyl, dialkylaminoalkyl, hydroxyalkyl, alkynyl, trialkylsilyl, alkylcycloalkyl, or cycloalkyl;
- $R^1$ and $R^2$ are independently selected from the group consisting of hydrogen, alkyl, haloalkyl, aralkyl, aryl, alkenyl, and dialkylaminoalkyl, with the proviso that $R^1$ and $R^2$ are not both methyl at the same time;
- X and Y are independently selected from the group consisting of halogen such as chloro, fluoro, bromo, iodo, alkoxy, dialkoxymethyl, alkyl, cyano, dialkylaminoalkyl carboxy, carboxamido, haloalkyl, haloalkylthio, allyl, aralkyl, cycloalkyl, aroyl, aralkoxy, alkanoyl, aryl, substituted aryl, alkylthio, alkylsulfonyl, haloalkylsulfonyl, alkylsulfinyl haloalkylsulfinyl, arylthio, haloalkoxy, amino, alkylamino, dialkylamino, hydroxy, carbamoyl, N-alkylcarbamoyl, N,N-dialkylcarbamoyl, nitro and dialkylsulfamoyl; is an integer selected from 0 (X or Y is hydrogen, respectively), 1, 2, 3 or 4.

Thus, it is an object of the present invention to provide anthracenimines of the above general description (I). It is also an obejct of this invention to provide pharmaceutical compositions comprising such anthracenimines and their non-toxic, pharmaceutically acceptable salt, ester and amide derivatives. Lastly, it is an object of the present invention to provide methods of treatment comprising administering the compounds and compositions of the present invention is situations where a minor tranquilizer and/or muscle relaxant and/or anticonvulsant effect is indicated and in the treatment of extrapyramidal disorders such as Parkinson's disease.

DETAILED DESCRIPTION OF THE INVENTION

With respect to the anthracenimines of the present invention (Structure I, above-depicted), the preferred embodiments are those wherein:
- $R^1$ and $R^2$ are independently selected from the group consisting of hydrogen, lower alkyl, having from 1 to about 6 carbon atoms, alkenyl having from 2 to about 6 carbon atoms, or dialkylaminoalkyl having from 3 to about 15 carbon atoms; with the proviso that $R^1$ and $R^2$ are not both methyl at the same time;
- is hydrogen or lower alkyl having from about 1 to about 6 carbon atoms, hydroxy lower alkyl having from 1 to about 6 carbon atoms, alkenyl having from 2 to about 6 carbon atoms, cycloalkyl having from 3 to about 6 carbon atoms, alkylcycloalkyl having from 4 to about 10 carbon atoms, benzyl (and X-or R-nuclear-substituted-benzyl), lower alkoxycarbonyl having 2 to about 7 carbon atoms or dialkylaminoalkyl having from 3 to about 15 carbon atoms;
- Y and X are independently selected from the group consisting of lower alkyl having from 1 to about 6 carbon atoms, fluoro, chloro, bromo, iodo, lower alkoxy having from 1 to about 6 carbon atoms, halo-substituted lower alkoxy having from 1 to about 6 carbon atoms, halo lower alkyl having from 1 to about 6 carbon atoms, cyano, carboxy, alkylthio, haloalkylsulfonyl and carboxamido; is an integer selected from 0 (X or Y is hydrogen, respectively), 1 or 2.

The most preferred anthracenimine embodiments of the present invention are those wherein
- $R^1$ and $R^2$ are selected from the group consisting of hydrogen lower alkenyl such as vinyl and the like, lower alkyl having from 1 to about 6 carbon atoms, such as methyl ethyl, propyl and the like, trifluoromethyl, di-loweralkylamino lower alkyl, such as dimethylaminopropyl and the like; with the proviso that $R^1$ and $R^2$ are not both methyl at the same time;
- R is hydrogen, benzyl or substituted benzyl, lower alkyl having from 1 to about 6 carbon atoms such as methyl, ethyl, propyl and the like, cyclopropyl, cyclobutyl, or di-loweralkylamino lower alkyl such as dimethylaminopropyl and the like;
- X and Y are chloro, bromo, iodo, lower alkoxy having from 1 to about 6 carbon atoms, lower alkyl having from 1 to about 6 carbon atoms, cyano, carboxy, carboxamido, trifluoromethoxy, trifluoromethyl, trifluoromethylsulfonyl, loweralkylthio such as methylthio and the like; is an integer selected from 0 (X or Y is hydrogen, respectively), 1 or 2.

In general, the anthracenimines of the present invention are prepared by reacting an appropriately substituted benzyne (III) with an appropriately substituted isoindole (Ia) according to the following reaction:

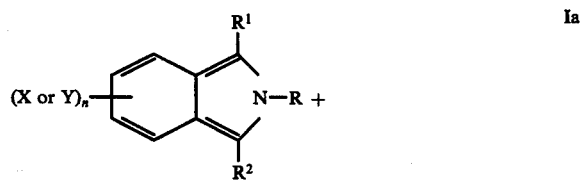

Ia

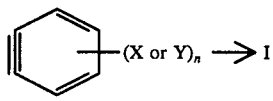

wherein all substituents are as previously defined and wherein the alternative indication of (X)$_n$ or (Y)$_n$ is permitted by the symmetry of the reaction and final product.

As a practical matter the benzyne reactant is generated in situ under conditions compatible with the ultimate Diels-Alder condensation with the isoindole. Preparation of such reactants and process conditions for the ultimate preparation of the anthracenimines of the present invention are described hereinafter.

ISOINDOLE PREPARATION

Many of the isoindoles useful in preparation of the anthracenimines of the present invention are known and readily available. Alternately, such isoindoles may be readily prepared by reacting an ortho-disubstituted benzene with a halogenating agent, such as N-bromosuccinimide (NBS), followed by reaction of the resulting α,α'-dihalogenated product with an N-substituted hydrazine (RNHNH$_2$); treatment of the latter with base provides the desired isoindole (Ia):

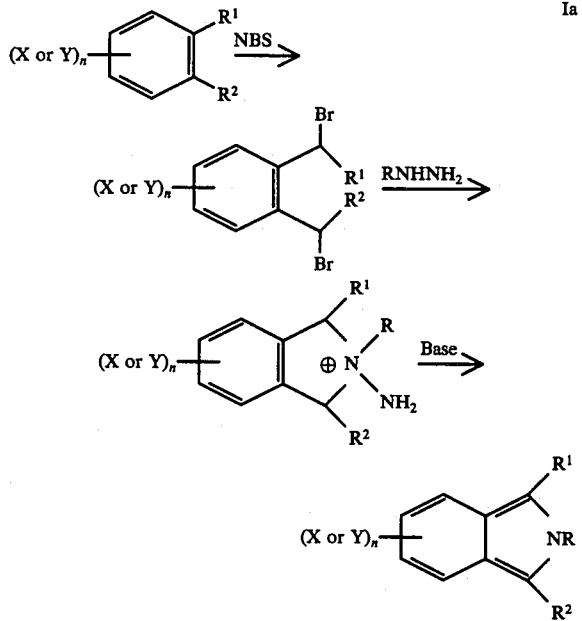

wherein all substituents are as previously defined.

Typically, the halogenating step in the preparation of the isoindole is conducted in the presence of an initiator such as benzoyl peroxide and the like under ultra violet irradiation. There is no criticality as to the reaction temperature, solvent system or the base used in the final step. Suitable solvents for the reaction include hydrocarbons such as hexane, benzene, and the like and halohydrocarbons such as carbontetrachloride, chlorobenzene and the like. Typically the reaction temperature is from about 25° C. to the reflux temperature; the noncritical base may be selected from sodium hydroxide, potassium hydroxide, potassium carbonate, and the like.

Another method of preparing suitably substituted isoindoles is set forth in the following scheme:

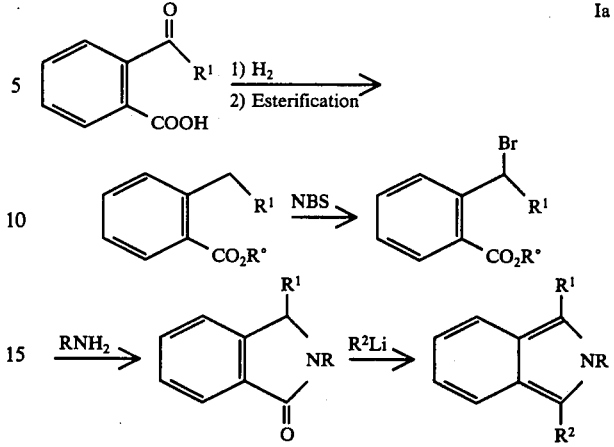

wherein all symbols have previously been defined and R° is any lower alkyl moiety such as methyl ethyl propyl, or the like. According to the above process, the o-acyl benzoic acid is first hydrogenated to reduce the carbonyl group by conventional procedures such as hydrogenation over palladium on carbon in aqueous sodium hydroxide solution; thereafter the free carboxy group is esterified by treating with diazomethane, sulfuric acid in methanol, or HCl in ethanol or other standard methods. Halogenation of the resulting substituted benzoic acid ester provides the above-illustrated α-halo intermediate. The halogenation may be effected, for example, by treating the ester with N-bromosuccinimide in CCl$_4$ at reflux. The treatment of the α-halo intermediate with the primary amine, RNH$_2$, in methanol, acetonitrile, ethanol, ether, THF or other polar organic solvent provides the above-illustrated phthalimidine which on treatment with R$^2$Li in ether, benzene, THF or other non-participating organic solvent at reflux or with a Grignard reagent, R$^2$MgX (X is halo such as chloro, bromo, or iodo) in anisole, THF, dibutyl ether or glyme at reflux provides the desired isoindole (Ia). Relative to the process illustrated immediately above, the esterification step may be eliminated according to the following procedure:

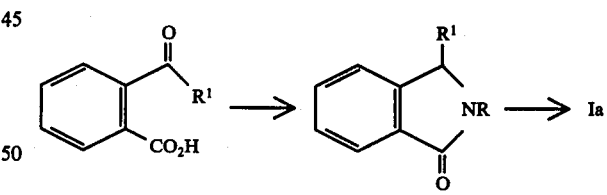

wherein the phthalimidine intermediate is obtained directly by treating the ortho-acylbennzoic acid with the primary amine, RNH$_2$, in the presence of NaCNBH$_3$ when protic solvents such as methanol, ethanol, and the like are employed or in the presence of NaBH$_4$, MgSO$_4$, and the hydrochloride of the primary amine when polar aprotic solvent such as acetonitrile, DMF, HMPA, and the like are employed. In either of the solvent systems there is not undue criticality as to reaction temperature, time and ratio of reactants; however, the following conditions are typically employed when the aprotic system is employed: the primary amine, as an equimolar mixture of the free base and its acid addition salt, is present in excess relative to the acylbenzoic acid, and the sodium borohydride is added portionwise over several hours to the solution of the amine and the acylbenzoic acid-MgSO$_4$ slurry.

Another method for preparing the above-mentioned isoindoles involves treating an ortho-diacylbenzene with a primary amine, $RNH_2$, in the presence of a reducing agent such as $NaBH_4$ or the like in a protic solvent at a reaction temperature of 20°–35° C. according too the following reaction scheme (all symbols are as previously defined):

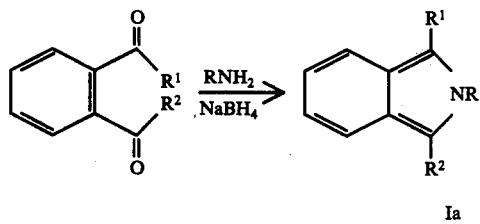

Ia

Another method for preparing the above-described isoindoles when either $R^1$ and $R^2$ is hydrogen involves treating phthalic anhydride with the primary amine, $RNH_2$, to yield a phthalimide intermediate which on reduction with, for example, zinc dust in glacial acetic acid yields the phthalimidine which on treatment with an appropriate lithium alkyl, $LiR^2$, or Grignard reagent, $R^2MgX$, yields the desired isoindole according to the following scheme:

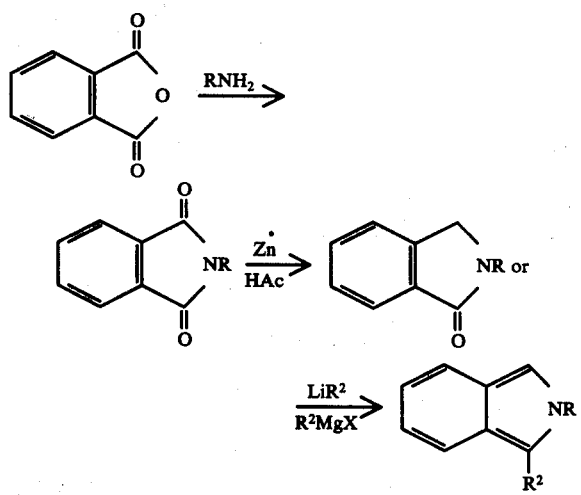

Yet another procedure for preparing the above-described isoindoles, especially when either $R^1$ or $R^2$ is hydrogen and when the benzenoid nucleus of the isoindole bears an electron releasing substituent (here denoted $X'$ which is selected from the group classed under X & Y, previously defined), such as alkyl, halogen or the like, involves Friedel-Crafts alkylation of a meta -$X'$ - substituted benzoic acid. The following equation summarizes this approach:

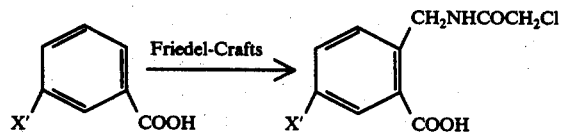

The immediate Friedel-Crafts product spontaneously cyclizes to form the phthalimidine intermediate which amy be N-alkylated by treating with RI in the presence of sodium hydride in a solvent system such as DMF of a 1:1 mixture of dimethylformamide and benzene. The resulting N-substituted phthalimidine on treatment with a suitable lithium alkyl($LiR^1$) or Grignard reagent ($R^1MgX$) as previously defined, yields the desired $R^1$ or $R^2$ substituted isoindole having the $X'$ substituted in the 5-position:

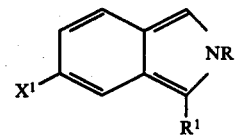

Suitable Friedel-Crafts reagents for the above reaction may be selected from N-hydroxymethylchloroacetamide and N-hydroxymethylphthalimide. The preferred Friedel-Crafts catalyst is concentrated $H_2SO_4$. Typically, the the reaction is conducted neat or in solvents such as $H_2SO_4$ and the like at a temperature of from about 0° C. to about 30° C.

Those skilled in the art will recognize that the above-disclosed processes may be employed individually or may be hybridized according to the most convenient path in the synthesis of the isoindoles needed for the preparation of the anthracenimines of the present invention.

BENZYNE PREPARATION

The transient benzyne reactant may be prepared by a variety of means including flash photolysis of a nuclear substituted benzene or by treatment of an orthodihalobenzene or a monohalo-substituted benzene with a strong base:

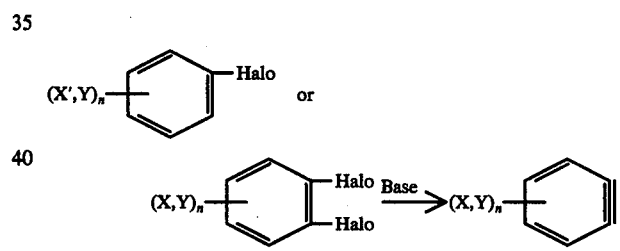

For purposes of the present invention it is preferred that the above illustrated benzyne be generated in situ for immediate Diels-Alder condensation with the isoindole. The following equation illustrates this reaction:

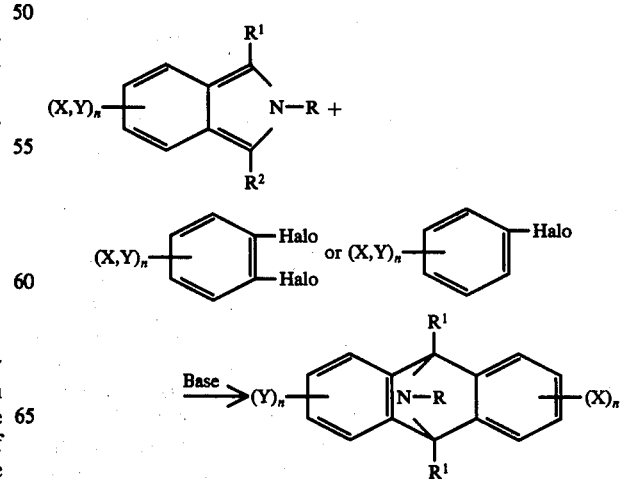

Suitable bases for the above reaction may be selected from the group consisting of alkali and alkaline earth metals and their corresponding oxides, hydrous oxides, alkoxides, alkali metal amides, alkali metal alkyls and the like. The most preferred bases are magnesium metal, and alkali metal alkyls such as methyllithium, butyllithium, phenyllithium, potassium-tertiary-butoxide, and alkali metal amides such as lithium diisopropylamide, lithium-2,2,6,6-tetramethylpiperidide, sodium amide and the like. There is no undue criticality as to the identity of the reaction solvent and suitable solvents may be selected from hydrocarbons such as benzene, hexane, cyclohexane and the like, oxygenated solvents such as ether, dioxane, tetrahydrofuran, anisole and the like. Typically the reaction is conducted at from about −70° C. to the reflux temperature.

A second method for the preparation of the anthracenimines of the present invention involves the Diels-Alder condensation of a substituted 1,3-butadiene and a naphthalenimine followed by aromatization of the newly formed 6-member ring by addition of bromine and elimination of HBr by treatment of the brominated intermediate with a base such as triethylamine:

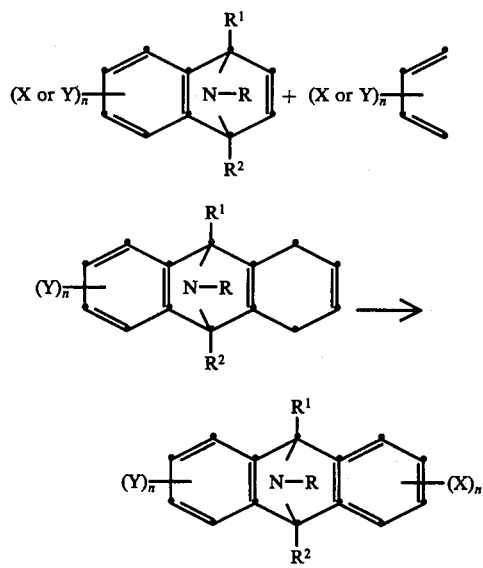

wherein all substituents have previously been defined. Such naphthalenimines, Ib, (substituted 1,4-dihydronaphthalen-1,4-imines) are disclosed in commonly assigned, copending U.S. Pat. Application Ser. No. 498,485, filed Aug. 19, 1974, which application is incorporated herein by reference. The subject naphthalenimines are useful as intermediates in the synthesis of the anthracenimines of the present invention. Typically, no solvent is required for the first step Diels-Alder reaction but suitable solvents for this step include THF, p-dichlorobenzene, toluene and the like at a reaction temperature of from about 25° C. to the reflux temperature, or at higher temperature when the reaction is conducted under pressure. The bromine addition reaction may be conducted in solvents such as acetic acid, $CCl_4$, chloroform, THF, benzene and the like. The final elimination reaction is typically performed in solvents such as benzene or THF in the presence of base, such as $(C_2H_5)_3N$, NaOH, or DBN (diazabicyclononene).

The third basic method for the preparation of the anthracenimines of the present invention involves derivatization operations upon the anthracenimine nucleus to provide certain embodiments of the present invention. The following reaction is illustrative of this approach:

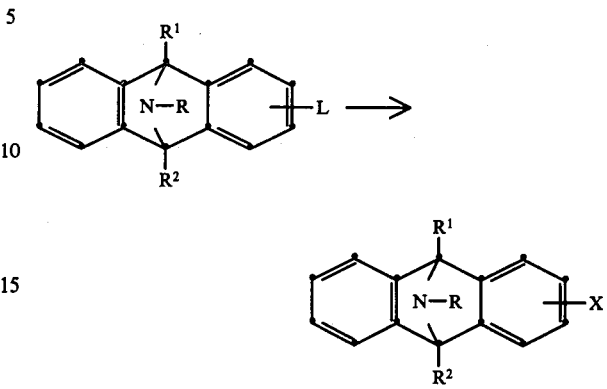

wherein for purposes of illustration the benzoid rings are shown to be substituted only with the leaving group L; however, it is not critical or even preferred that L be the sole benzoid substituent for this aspect of the invention. L may be any chemically modifiable group such as amino, hydroxy, bromo, iodo, chloro and the like which may be transformed to function X by known procedures. X is as previously defined and, especially for this aspect of the invention, embraces radicals such as cyano, trifluoromethylthio, methylthio, and the like. Suitable solvents for this process aspect of the invention include dimethylformamide, hexamethylphosphoramide (HMPA), THF, quinoxaline and the like. Typically the reaction is conducted at from about 25° C. to the reflux temperature.

Other derivatization reactions which do not involve critical reaction parameters and which are representatively depicted by the examples which follow include: N-alkylation; N-acylation ahd reduction; reductive alkylation; and electrophilic substitution on the benzoid nucleii.

Also included within the scope of the present invention are non-toxic pharmaceutically acceptable salt, ester and amide derivatives of I. Acid addition salts are preferred. Such acid addition salts of the anthracenimine compounds are formed by mixing a solution of the anthracenimine compounds with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid and the like.

In the method of treatment aspect of the present invention, the instant minor tranquilizer anthracenimines are capable of producing anxiety relief without causing excessive sedation or sleep at a unit dosage level of from about 0.1 to about 500 mg. per kilogram of body weight, or at a daily dosage level of from about 0.4 to about 2,000 mg. per kilogram of body weight. In addition, the anthracenimines of the present invention are useful as muscle relaxants, anticonvulsants and in the treatment of extrapyramidal disorders when indicated at comparable dosage levels. Of course, it is understood that the exact treatment level will depend upon the case history of the animal or human individual being treated and in the last analysis the precise treatment level falling within the above guidelines is left to the discretion of the therapist.

Also included within the scope of the present invention are pharmaceutical compositions comprising such anthracenimines. Preferably these compositions are in unit dosage forms such as tablets, pills, capsules, powders, granules, sterile parenteral solutions or suspensions, and the like. For preparing solid compositions such as tablets, the principal active ingredient is mixed with a pharmaceutical carrier, i.e., conventional tableting ingredients such as corn starch, lactose, sucrose, sorbitol, talc, stearic acid, magnesium stearate, dicalcium phosphate, gums, and other pharmaceutical diluents, e.g., water, to form a solid preformulation composition containing a homogeneous mixture of an anthracenimine of the present invention, or a non-toxic pharmaceutically acceptable salt, ester or amide derivative thereof. When referring to these preformulation compositions as homogeneous, it is meant that the active ingredient, i.e., the anthracenimine, is dispersed evenly throughout the composition so that the composition may be readily subdivided into equally effective unit dosage forms such as tablets, pills, capsules, and the like. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action of the instant anthracenimines. For example, the tablet or pill can comprise an inner dosage and an outer dosage component, the latter being in the form of an envelope over the former. The two components can be separated by an enteric layer which serves to resist disintegration in the stomach and permits the inner component to pass intact into duodenum or to be delayed in release. A variety of materials can be used for such enteric layers or coatings, such materials including a number of polymeric acids or mixtures of polymeric acids with such materials as shellac, shellac and cetyl alcohol, cellulose acetate, and the like.

The liquid forms in which the novel composition of the present invention may be incorporated for administration orally or by injection include aqueous solutions, suitably flavored syrups, aqueous or oil suspensions, flavored emulsions with edible oils such as cottonseed oil, sesame oil, coconut oil, peanut oil and the like, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, gelatin and the like.

The pharmaceutical anthracenimine formulations of the present invention can be administered orally, parenterally, or rectally. Orally, they may be administered in tablets, capsules, suspensions or syrups, the preferred dosage form being a compressed tablet containing from 0.1 to about 500 mg. of the active ingredient. The optimum dosage depends of course on the dosage form being used and the type and severity of the condition being treated. In any specific case, as previously mentioned, the appropriate dosage selected will further depend on factors of the patient which may influence response to the drug, for example, general health, age, weight, and the desired effect.

The following Examples representatively illustrate, but do not limit, the product, process, method of treatment, or compositional aspects of the present invention.

EXAMPLE 1

2-Bromo-11-methyl-9,10-dihydroanthracen-9,10-imine

Ethyl ether (60 ml.) and 1.9 molar butyllithium in ether (11.3 ml.) are added to a dry flask under $N_2$ and cooled to $-70°$ C. in a dry ice/acetone bath. To this solution is added, dropwise with stirring, a solution of 4.4 g. of 1-bromo-2-fluorobenzene in ether (20 ml.) followed by a solution of 5.75 g. of 5-bromo-2-methylisoindole in ether (25 ml.). The cooling bath is removed and stirring continued for 3 hours. The reaction mixture is poured into water and extracted with chloroform (3 × 100 ml.). The combined chloroform extracts are dried over $Na_2SO_4$, filtered and concentrated under reduced pressure. The concentrate is chromatographed on silica gel eluting with chloroform. The crude product obtained from the eluant is treated with fumaric acid in isopropanol to obtain the fumaric acid salt, m.p. 168–170° C. after recrystallization from an equal volume mixture of isopropanol and ethyl acetate.

Elemental analysis for: $C_{15}H_{12}BrN.1.5 \ C_4H_4O_4$: Calcd.: C, 54.80; H, 3.93; N, 3.04. Found: C, 54.97; H, 4.12; N, 2.87.

EXAMPLE 2

2-Methoxy-11-methyl-9,10-dihydroanthracen-9,10-imine

Magnesium metal (0.78 g., 0.032 mole), dry THF (30ml.) and N-methylisoindole (4.2 g., 0.032 mole) are placed in a dry flask under $N_2$ and heated under reflux with stirring. To this mixture is added dropwise over 30 minutes a solution of 2-iodo-4-methoxybromobenzene (10 g., 0.032 mole) in 30 ml. of THF. Heating is continued for 1.5 hours and the solvent is then evaporated under reduced pressure. The residue is treated with 200 ml. of benzene and 5 ml. of water and then filtered. The filtrate is evaporated and the concentrate chromatographed on silica gel using chloroform as eluant. The eluant is concentrated and then extracted with hot hexane. On cooling the hexane extract, crystals of 2-methoxy-11-methyl-9,10-dihydroanthracen-9,10-imine are obtained, m.p. 94–96° C.

Elemental analysis of $C_{16}H_{15}NO$: Calcd.: C, 80.95; H, 6.37; N, 5.90; Found: C, 80.24; H, 6.49; N, 5.89.

EXAMPLE 3

9,10-Diethyl-11-methyl-9,10-dihydroanthracen-9,10-imine

Step A: 1,3-diethyl-2-methylisoindole

A mixture of 0.374 mole of o-dipropylbenzene, 146 g. (0.822 mole) of N-bromosuccinimide, 0.1 g. of benzoyl peroxide, and 800 ml. of carbon tetrachloride is heated under reflux with stirring and ultraviolet irradiation until the reaction is complete. The precipitated succinimide is filtered, washed with carbon tetrachloride, and the filtrate is evaporated to dryness under reduced pressure. The residual α,α'-dibromo-o-dipropylbenzene is dissolved in 800 ml. of absolute ether. To the stirred solution under nitrogen is added dropwise a solution of 40 g. (0.87 mole) of methyl hydrazine in 50 ml. of absolute ether. A gummy precipitate separates. After 3 hours of stirring and an overnight period of standing, the ether is decanted. The residue dissolved in 625 ml. of water is treated with 375 ml. of 40% sodium hydroxide solution and the mixture is stirred at reflux for 1.5 hours. After cooling, the precipitate of the crude product is collected, washed with water, and dissolved in 600 ml. of ether. The ether solution is washed repeatedly with water and dried over anhydrous magnesium sulfate with stirring and cooling in an ice bath. The filtered solution is evaporated under reduced pressure and the residual dark yellow solid is triturated with petroleum ether, filtered and dried in vacuo to yield 1,3-diethyl-2-methylisoindole.

Step B:
9,10-diethyl-11-methyl-9,10-dihydroanthracen-9,10-imine

In a dry apparatus maintained in a nitrogen atmosphere, 1.7 g. (0.07 moles) of magnesium turnings are suspended in 10 ml. of dry tetrahydrofuran and the mixture is heated to refluxing. The reaction is initiated by the addition of a few drops of 2-fluorobromobenzene and a mixture of 0.06 mole of 1,3-diethyl-2-methylisoindole and 12.3 g. (0.07 mole) of 2-fluorobromobenzene in 70 ml. of dry tetrahydrofuran is added dropwise over 1 hour. Stirring at reflux is continued for 2 hours. The cooled mixture is hydrolyzed by the dropwise addition of 25 ml. of water and the organic layer is decanted. Solvent is evaporated under reduced pressure and the residual dark oil is dissolved in benzene. The solution is filtered through diatomaceous earth, diluted with ether, and washed with water. The dried extract is evaporated to dryness under reduced pressure, leaving crude 9,10-diethyl-11-methyl-9,10-dihydroanthracen-9,10-imine as a residual dark red oil which is converted to the fumaric acid salt by dissolving it in 30 ml. of ethylacetate and adding to a solution of 10.4 g. (0.09 mole) of fumaric acid in 100 ml. of absolute methanol. Dilution with 320 ml. of ethyl acetate and seeding precipitates the crude salt. Two recrystallizations from methanol:ethyl acetate (1:1), using decolorizing charcoal, gives the fumarate salt of 9,10-diethyl-11-methyl-9,10-dihydroanthracen-9,10-imine, m.p. 173°–175° C.

Following the procedure of Example 3, Step A, except that the o-dipropylbenzene of Example 3 is replaced by an equivalent amount of: 2-ethyltoluene, 2-propylethylbenzene, o-bis($\beta,\beta,\beta$-trifluoroethyl)benzene, o-dibutylbenzene and 2-butyl-propylbenzene, respectively, there is obtained 1,2-dimethylisoindole; 1,2-dimethyl-3-ethylisoindole; 1,3-bis(trifluoromethyl)-2-methylisoindole; 1,3-dipropyl-2-methylisoindole; and 1-ethyl-2-methyl-3-propylisoindole, respectively.

When the above-listed isoindoles individually replace the 1,3-diethyl-2-methylisoindole of Example 3, Step B, there is obtained: 9,11-dimethyl-9,10-dihydroanthracen-9,10-imine; 9,11-dimethyl-10-ethyl-9,10-dihydroanthracen-9,10-imine; 9,10-trifluoromethyl-11-methyl-9,10-dihydroanthracen-9,10-imine; 11-methyl-9,10-dipropyl-9,10-dihydroanthracen-9,10-imine and 11-methyl-9-ethyl-10-propyl-9,10-dihydroanthracen-9,10-imine, respectively.

Following the procedure of Example 3, Step A, except that the o-dipropylbenzene of Example 3 is replaced by an equivalent amount of: 4-chloro-; 4-iodo-; and 4-bromo-1,2-dipropylbenzene and the methylhydrazine is replaced by an equivalent amount of propylhydrazine; cyclopropylhydrazine; and $\gamma$-THP-oxy-propylhydrazine, there is obtained 5-chloro, 5-iodo, and 5-bromo-2-propyl-1,3-diethylisoindole; 5-chloro-; 5-iodo-; and 5-bromo-2-cyclopropyl-1,3-diethylisoindole; and 5-chloro-; 5-iodo-; and 5-bromo-2-$\gamma$-THP-oxy-propyl-1,3-diethylisoindole, respectively; wherein THP represents tetrahydropyranyloxy.

When the above-listed isoindoles individually replace the 1,3-diethyl-2-methylisoindole of Example 3, Step B, there is obtained: 2-chloro-; 2-iodo-; and 2-bromo-11-propyl-9,10-diethyl-9,10-dihydroanthracen-9,10-imine; 2-chloro-; 2-iodo-; and 2-bromo-11-cyclopropyl-9,10-diethyl-9,10-dihydroanthracen-9,10-imine; and 2-chloro-; 2-iodo-; and 2-bromo-11-[$\gamma$-THP-oxy-propyl]-9,10-diethyl-9,10-dihydroanthracen-9,10-imine, respectively; mild acid hydrolysis of the last three mentioned compounds provides 2-chloro-; 2-iodo-; and 2-bromo-11-hydroxypropyl-9,10-diethyl-9,10-dihydroanthracen-9,10-imine, respectively.

EXAMPLE 4

2,11-dimethyl-9,10-diethyl-9,10-dihydroanthrcen-9,10-imine

In a dry apparatus maintained in a nitrogen atmosphere, 0.77 g. (0.0315 moles) of magnesium turnings are suspended in a solution of 0.031 mole of 1,3-diethyl-2-methylisoindole in 30 ml. of dry tetrahydrofuran and the mixture is heated to reflux. A solution of 6.45 g. (0.0315 mole) of 3-bromo-4-chlorotoluene in 25 ml. of dry tetrahydrofuran is added dropwise over 30 minutes. Stirring at reflux is continued for 6 hours. The cooled mixture is hydrolyzed by the dropwise addition of 5 ml. of water and the organic layer is decanted. The residual precipitate is washed repeatedly with methylene chloride. Evaporation of the combined organic extracts under reduced pressure leaves a dark oil that is triturated with ether. The resulting insoluble purple solid is filtered and the filtrate evaporated to dryness in vacuo. The residual black oil is chromatographed on a column of 235 g. of silica gel, the 11-dimethyl-9,10-diethyl-9,10-dihydroanthracen-9,10-imine being eluted with chloroform. The fractions comprising the third to sixth liter of eluant are combined and evaporated. The residual oil is triturated with hexane and filtered from insoluble material. Evaporation of the filtrate under reduced pressure leaves crude 2,11-dimethyl-9,10-diethyl-9,10-dihydroanthracen-9,10-imine as a residual dark oil, which is converted to the hydrogen fumarate salt by dissolving in the minimum amount of absolute methanol and adding to a saturated solution of 3.9 g. (0.0322 mole) of fumaric acid in absolute methanol. Evaporation of the solution and trituration of the residual blue solid with ether gives the crude salt. Three recrystallizations from isopropyl alcohol yields pure 2,11-dimethyl-9,10-diethyl-9,10-dihydroanthracen-9,10-imine fumarate.

EXAMPLE 5

2-Chloro-9,10-diethyl-11-methyl-9,10-dihydroanthracen-9,10-imine

Following procedure described in Example 3, 2-chloro-9,10-diethyl-11-methyl-9,10-dihydroanthracen-9,10-imine is obtained from 1,3-diethyl-2-methylisoindole and 2,5-dichlorobromobenzene. The resulting crude ethersoluble oily fraction is triturated with hexane and filtered from insoluble material. Evaporation of the hexane filtrate leaves a dark oil that is chromatographed on a column of silica gel, the product being eluted with chloroform. Fractions containing 2-chloro-9,10-dihydro-9,10-diethyl-11-methylanthracen-9,10-imine as determined by thin layer chromatography on fluorescent silica gel are combined and evaporated. The residue is converted to the hydrogen oxalate hydrate salt by treating a saturated solution thereof in 95% ethanol with a saturated solution of oxalic acid in 95% ethanol. Addition of several drops of water and dilution with absolute ether precipitates the salt. Recrystallization from acetone using decolorizing charcoal, yields 2-chloro-9,10-diethyl-11-methyl-9,10-dihyroanthracen-9,10-imine hydrogen oxalate hydrate.

EXAMPLE 6

1-Fluoro-9,10-diethyl-11-methyl-9,10-dihydroanthracen-9,10-imine

Following procedure described in Example 3, 1-fluoro-9,10-diethyl-11-methyl-9,10-dihydroanthracen-9,10-imine is obtained from 1,3-diethyl-2-methylisoindole and 2,6-difluorobromobenzene. The resulting crude, ethersoluble, black oil is triturated with hexane, filtered from insoluble material, and the filtrate is evaporated to dryness in vacuo. The residual dark oil is charomatographed on a column of silica gel, the product being eluted with chloroform. The fractions containing 1-fluoro-9,10-diethyl-11-methyl-9,10-dihydroanthracen-9,10-imine as determined by nuclear magnetic resonance spectra are combined and evaporated. The residual oily solid is triturated with petroleum ether to yield 1-fluoro-9,10-diethyl-11-methyl-9,10-dihydroanthracen-9,10-imine as an insoluble brown solid, which is converted to the hydrogen oxalate salt by treating a saturated isopropyl alcohol solution thereof with a saturated isopropyl alcohol solution of oxalic acid. The salt precipitates and is recrystallized from isopropyl alochol to obtain 1-fluoro-9,10-diethyl-11-methyl-9,10-dihydroanthracen-9,10-imine-hydrogen oxalate.

EXAMPLE 7

2-Methoxy-9,10-diethyl-11-methyl-9,10-dihydroanthracen-9,10-imine

Following the procedure described in Example 3, 2-methoxy-9,10-diethyl-11-methyl-9,10-dihydroanthracen-9,10-imine is obtained from 1,3-diethyl-2-methylisoindole and 4-bromo-3-iodoanisole. The crude, ether-soluble, dark brown oil is triturated with hexane, filtered from insoluble material, and the filtrate is evaporated to dryness in vacuo. The residual dark oil is triturated with an aqueous solution of excess maleic acid and the mixture partitioned between water and ether. The aqueous phase is separated, made strongly basic with aqueous sodium hydroxide and the oily base is extracted into benzene:ether (1:1). Evaporation of the washed and dried extract under reduced pressure leaves 2-methoxy-9,10-diethyl-11-methyl-9,10-dihydroanthracen-9,10-imine as the residual dark oil. Purification is effected by column chromatography on silica gel, the product being eluted with chloroform. Fractions containing 2-methoxy-9,10-diethyl-11-methyl-9,10-dihydroanthracen-9,10-imine as determined by nuclear magnetic resonance spectra are combined and evaporated. The residue is subjected to short path distillation to obtain 2-methoxy-9,10-diethyl-11-methyl-9,10-dihydroanthracen-9,10-imine.

The base is converted to the hydrogen oxalate salt by dissolving it in methanol saturated with oxalic acid. Dilution with absolute ether precipitates the salt as a gum which crystallizes on trituration with 95% ethanol. Recrystallization from acetone gives 9,10-dihydro-2-methoxy-9,10-diethyl-11-methylanthracen-9,10-imine hydrogen oxalate hydrate.

EXAMPLE 8

9,10-Diethyl-1,11-dimethyl-9,10-dihydroanthracen-9,10-imine

Following the procedure described in Example 3, 9,10-diethyl-1,11-dimethyl-9,10-dihydroanthracen-9,10-imine is obtained from 1,3-diethyl-2-methylisoindole and 2-bromo-3-chlorotoluene. The crude oily product is triturated with hexane and filtered from insoluble material. Evaporation of the hexane filtrate leaves a yellow oil that is dissolved in methanol and treated with a solution of an excess of maleic acid in methanol. Dilution with absolute ether precipitates a dark gummy solid that is dissolved in water. The filtered solution is cooled, made strongly basic with aqueous sodium hydroxide, and the oily base is extracted into ether. Evaporation of the washed and dried extract under reduced pressure leaves a dark yellow oil that partially solidifies on standing. Trituration of this residue with ice-cold petroleum ether yields 9,10-diethyl-1,11-dimethyl-9,10-dihydroanthracen-9,10-imine as a yellow solid. The hydrogen oxalate salt is obtained by treating a saturated isopropyl alcohol solution of 9,10-diethyl-1,11-dimethyl-9,10-dihydroanthracen-9,10-imine with a saturated solution of oxalic acid in isopropyl alcohol. Dilution with absolute ether precipitates the salt which is recrystallized from absolute ethanol to obtain 9,10-diethyl-1,11-dimethyl-9,10-dihydroanthracen-9,10-imine hydrogen oxalate.

EXAMPLE 9

2-Trifluoromethyl-9,10-diethyl-11-methyl-9,10-dihydroanthracen-9,10-imine

Following the procedure described in Example 3, 2-trifluoromethyl-9,10-diethyl-11-methyl-9,10-dihydroanthracen-9,10-imine is obtained from 1,3-diethyl-2-methylisoindole and 2-bromo-4-trifluoromethylchlorobenzene. The crude, hexane-soluble, oily product is purified by column chromatography on alumina, the product being eluted with benzene. Fractions containing the major component on a fluorescent alumina thin layer plate developed with benzene are combined. Evaporation of the solvent under reduced pressure leaves an oil that is subjected to short path distillation to obtain 2-trifluoromethyl-9,10-diethyl-11-methyl-9,10-dihydroanthracen-9,10-imine.

The base is converted to the hydrogen oxalate salt by dissolving it in 95% ethanol saturated with oxalic acid containing a few drops of water. Dilution with absolute ether precipitates the salt which is recrystallized from acetone-ether to obtain 9,10-dihydro-2-trifluoromethyl-9,10-diethyl-11-methylanthracen-9,10-imine hydrogen oxalate hydrate.

EXAMPLE 10

2-Fluoro-9,10-diethyl-11-methyl-9,10-dihydroanthracen-9,10-imino

Following the procedure described in Example 3, 2-fluoro-9,10-diethyl-11-methyl-9,10-dihydroanthracen-9,10-imine is obtained from 1,3-diethyl-2-methylisoindole and 2,4-difluorobromobenzene. The crude, dark oily product is triturated with hexane and filtered from insoluble material. Evaporation of the hexane filtrate leaves a brown oil that is purified by column chromatography on silica gel, the product being eluted with chloroform. Fractions containing product as determined by nuclear magnetic resonance spectra are combined. Evaporation of the solvent under reduced pressure leaves the product as a brown oil, which is converted to the fumaric acid salt by dissolving the oil in the minimum volume of ethyl acetate and adding a saturated solution of fumaric acid in methanol. Dilution with ethyl acetate and seeding precipitates the salt. Recrystallizations from an equal volume mixture of methanol and ethyl acetate and from isopropyl alcohol give 2-fluoro-9,10-diethyl-11-methyl-9,10-dihydroanthracen-9,10-imine fumaric acid salt.

EXAMPLE 11

1,3-Difluoro-11-methyl-9,10-dihydroanthracen-9,10-imine

In a dry apparatus maintained in a nitrogen atmosphere, a solution of 10.55 g. (0.05 mole) of 1-bromo-2,4,6-trifluoro-benzene in 10 ml. of absolute ether is added dropwise to a stirred solution of 25 ml. of 2.2M. n-butyllithium in hexane cooled in a dry ice-acetone bath. A solution of 6.6 g. (0.05 mole) of 2-methylisoindole in 100 ml. of absolute ether is added dropwise and stirring is continued overnight at 25° C. The mixture is hydrolyzed by the dropwise addition of 15 ml. of water. After separation and re-extraction of the aqueous phase with ether, the combined, washed and dried ether extracts are evaporated under reduced pressure. The residual dark brown oil is purified by column chromatography on 600 g. of silica gel, the product, 1,3-difluoro-11-methyl-9,10-dihydroanthracen-9,10-imine, being eluted with chloroform. Fractions comprising the sixth liter of eluant and containing a component of $R_f 0.2$ on a fluorescent silica thin layer plate developed with chloroform are combined. Evaporation of the solvent under reduced pressure leaves a brown oil that is triturated with hexane. The insoluble material is filtered and the filtrate evaporated to dryness in vacuo, leaving a dark oil that is dissolved in ether. This solution is treated with a solution of 2.5 g. of fumaric acid in 25 ml. of absolute ethanol and evaporated to dryness in vacuo. The residue is triturated with water and the insoluble material is filtered. The aqueous filtrate is made strongly basic with 40% sodium hydroxide and the oily base is extracted into benzene. Evaporation of the washed and dried extract under reduced pressure leaves 1.4 g. of 1,3-difluoro-11-methyl-9,10-dihydroanthracen-9,10-imine as a dark yellow oil, which is converted to the hyrogen oxalate salt by treating a solution thereof in the minimum volume of absolute ether with a saturated solution of oxalic acid in absolute ethanol. The salt precipitates and is recrystallized from an equal volume mixture of ethanol and ether to obtain 0.83 g. of 1,3-difluoro-11-methyl-9,10-dihydroanthracen-9,10-imine hydrogen oxalate as white crystals, m.p. 151°–153° C.

Elemental analysis for $C_{15}H_{11}F_2N.C_2H_2O_4$: Calcd.: C,61.26; H, 3.93; N, 4.20., Found: C, 61.60; H, 4.21; N, 4.23.

EXAMPLE 12

5-Bromo-1,3-diethyl-2-methylisoindole

Following the procedure described in Example 3, 3,4-dipropylbromobenzene is converted to 5-bromo-1,3-diethyl-2-methylisoindole. The crude solid is purified by sublimation.

EXAMPLE 13

2-Bromo-9,10-diethyl-11-methyl-9,10-dihydroanthracen-9,10-imine

Following the procedure described in Example 11, 2-bromo-9,10-diethyl-11-methyl-9,10-dihydroanthracen-9,10-imine is obtained from 5-bromo-1,3-diethyl-2-methylisoindole and 2-bromofluorobenzene. The crude, hexane-soluble, oily product is purified by column chromatography on silica gel. The product is eluted with chloroform, fractions containing a major component on a fluorescent alumina thin layer plate developed with benzene being combined. Evaporation of the solvent under reduced pressure leaves an oil that is purified further by rechromatographing on a column of silica gel. The product is eluted with 0.5% methanol in chloroform and fractions containing essentially a single component on a fluorescent silica thin layer plate developed with methanol:chloroform (2:98) are combined. Evaporation of the solvent under reduced pressure leaves 2-bromo-9,10-diethyl-11-methyl-9,10-dihydroanthracen-9,10-imine as an oil, which is converted to the hydrogen oxalate salt by treating a saturated solution thereof in absolute ethanol with a saturated solution of oxalic acid in absolute ethanol. Dilution with acetone and absolute ether precipitates the salt. Two recrystallizations from acetone yield 2-bromo-9,10-diethyl-11-methyl-9,10-dihydroanthracan-9,10-imine hydrogen oxalate hydrate.

EXAMPLE 14

2-Cyano-9,10-diethyl-11-methyl-9,10-dihydroanthracen-9,10-imine

A stirred mixture of 0.001 mole of 2-bromo-9,10-diethyl-11-methyl-9,10-dihydroanthracen-9,10-imine, 0.089 g. (0.001 mole) of cuprous cyanide and 7 ml. of dry dimethylformamide is heated at reflux for 6 hours. The mixture is diluted with benzene and filtered through diatomaceous earth. Evaporation of the filtrate in vacuo leaves a dark brown oily residue that is purified by column chromotography on silica gel. The product is eluted with chloroform and fractions containing essentially a single component on a fluorescent silica thin layer plate developed with methanol:chloroform (2:98) are combined. evaporation of the solvent under reduced pressure leaves the 2-cyano-9,10-diethyl-11-methyl-9,10-dihydroanthracen-9,10-imine as a residual oil.

EXAMPLE 15

2-Carboxy-9,10-diethyl-11-methyl-9,10-dihydroanthracen-9,10-imine

To a stirred solution of 0.005 mole of 2-bromo-9,10-diethyl-11-methyl-9,10-dihydroanthracen-9,10-imine in 5 ml. of absolute ether under nitrogen and cooled in an ice-salt bath, is added dropwise 2.3 ml. of 2.2 M n-butyllithium in hexane. The mixture is stirred at 0° C. for 40 minutes, then at 25° C. for 20 minutes. After again cooling the mixture to 0° C., carbon dioxide is bubbled in for 30 minutes. The mixture then is hydrolyzed by the dropwise addition of water and the aqueous phase is separated. Neutralization with dilute hydrochloric acid precipitates 2-carboxy-9,10-diethyl-11-methyl-9,10-dihydroanthracen-9,10-imine.

EXAMPLE 16

(+) 2,11-dimethyl-9,10,diethyl-9,10-dihydroanthracen-9,10-imine

Racemic 2,11-dimethyl-9,10-diethyl-9,10-dihydroanthracen-9,10-imine, (0.0137 mole) and 5.27 g. (0.0137 mole) of (+) di-p-toluoyl-1-tartaric acid are dissolved in 17 ml. of acetone. The solution is diluted with 7 ml. of absolute ether and seeded. After several hours of standing at room temperature, the crystalline salt is collected and recrystallized repeatedly from acetone-ether to constant rotation. The product is dissolved in a minimum volume of hot methanol and the solution stirred with an ice-cold mixture of a solution of 20 g. of potassium carbonate in 30 ml. of water and 30 ml. of hexane. The aqueous layer is separated and re-extracted twice with hexane. The combined, washed and dried hexane extracts are evaporated to dryness under reduced pressure leaving (+) 2,11-dimethyl-9,10-diethyl-9,10-dydroanthracen-9,10-imine as a residual oil.

The base is converted to the hydrogen fumarate salt by dissolving it in the minimum volume of methanol saturated with fumaric acid. Dilution with ether precipitates (+) 2,11-dimethyl-9,10-diethyl-9,10-dihydroanthracen-9,10-imine hydrogen fumarate.

EXAMPLE 17

(−) 2,11-dimethyl-9,10-diethyl-9,10-dihydroanthracen-9,10-imine

The acetone-ether mother liquor from the initial crystallization of the (+)-isomer is evaporated to dryness under reduced pressure. A suspension of the residual glass in benzene is stirred with an ice-cold solution of 20 g. of potassium carbonate in 30 ml. of water. The aqueous layer is separated and re-extracted twice with benzene. Evaporation of the combined, washed and dried benzene extracts under reduces pressure leaves the optically impure (−)-base as the residual oil. This product and 1.75 g. (0.0045 mole) of (−) di-p-toluoyl-d-tartaric acid are dissolved in 9 ml. of absolute ethanol. Dilution with 50 ml. of absolute ether precipitates a crystalline salt which is recrystallized repeatedly from acetone-ether to constant rotation. The product is suspended in hexane and the mixture stirred with a solution of 10 g. of sodium carbonate in 20 ml. of water. The aqueous layer is separated and re-extracted twice with hexane. The combined, washed and dried hexane extracts are evaporated to dryness under reduced pressure leaving (−) 2,11-dimethyl-9,10-diethyl-9,10-dihydroanthracen-9,10-imine as the residual oil.

The base is converted to the hydrogen fumarate salt by dissolving it in methanol saturated with fumaric acid. Dilution with ether precipitates (−)-2,11-dimethyl-9,10-diethyl-9,10-dihydroanthracen-9,10-imine hydrogen fumarate.

EXAMPLE 18

2-Methylthio-9,10-diethyl-11-methyl-9,10-dihydroanthracen-9,10-imine

In a dry apparatus maintained in a nitrogen atmosphere, a solution of 23.4 ml. of 1.8 M methyllithium in ether is added dropwise to a stirred solution of 5.64 g. (0.04 mole) of 2,2,6,6-tetramethylpiperidine in 25 ml. of dry tetrahydrofuran. The resulting solution of lithium tetramethylpiperidine is added dropwise to a stirred solution of 0.036 mole of 1,3-diethyl-2-methylisoindole and 6.34 g. (0.04 mole) of (4-chlorophenyl)methylsulfide in 40 ml. of dry tetrahydrofuran at room temperature and in a nitrogen atmosphere. Stirring is continued at reflux for 15 hours. The cooled mixture is poured into 150 ml. of saturated ammonium chloride solution containing 2 ml. of concentrated ammonium hydroxide. After separation and re-extraction of the aqueous phase with ether, the combined organic extracts are evaporated under reduced pressure. The residual dark oil is triturated with hexane and filtered from insoluble material. Evaporation of the hexane filtrate leaves the crude product as the residual dark oil which is purified by column chromatography on silica gel, the product being eluted with chloroform. Fractions containing a basic component of common $R_f$ value on a fluorescent silica thin layer plate developed with chloroform-methanol (98:2) are combined. Evaporation of the solvent under reduced pressure leaves a dark oil which is rechromatographed on 300 g. of silica gel, the product being eluted with chloroform to obtain a dark yellow oil after evaporation of solvent.

The base is converted to the hydrogen oxalate salt by dissolving it in acetone saturated with oxalic acid containing a few drops of water. Dilution with absolute ether precipitates the salt which is recrystallized twice from acetone to obtain 2-methylthio-9,10-diethyl-11-methyl-9,10-dihydroanthracen-9,10-imine hydrogen oxalate hydrate.

EXAMPLE 19

Following the procedure of Example 18, the following compounds are obtained:
  2-Bromo-11-propyl-9,10dimethyl-9,10-dihydroanthracen-9,10-imine;
  2-Chloro-11-propyl-9,10-diethyl-9,10-dihydroanthracen-9,10-imine;
  2-Iodo-11-propyl-9,10-diethyl-9,10-dihydroanthracen-9,10-imine;
  2-Bromo-11-cyclopropyl-9,10-diethyl-9,10-dihydroanthracen-9,10-imine;
  2-Chloro-11-cyclopropyl-9,10-diethyl-9,10-dihydroanthracen-9,10-imine;
  2-Iodo-11-cyclopropyl-9,10-diethyl-9,10-dihydroanthracen-9,10-imine;
  2-Bromo-11-(3-hydroxypropyl)-9,10-diethyl-9,10-dihydroanthracen-9,10-imine;
  2-chloro-11-(3-hydroxypropyl)-9,10-diethyl-9,10-dihydroanthracen-9,10-imine;
  2-Iodo-11-(3-hydroxypropyl)-9,10-diethyl-9,10-dihydroanthracen-9,10-imine; respectively,
when the (4-chlorophenyl) methylsulfide of Example 17 is replaced by an equivalent amount of 1,4-dibromobenzene; 1,4-dichlorobenzene; 1,4-diiodobenzene and the 1,3-diethyl-2-methylisoindole is replaced by an equivalent amount of 1,3-diethyl-2-propyl-isoindole; 1,3-dimethyl-2-cyclopropylisoindole; and 1,3-diethyl-2-[3-THP-oxy-propyl]-isoindole, respectively. The above-mentioned 11-[3-hydroxypropyl] species are obtained from the corresponding 11-[3-THP-oxy-propyl] species by acid hydrolysis according to the procedure of Example 3.

EXAMPLE 20

1-Isopropyl-9,10-diethyl-11-methyl-9,10-dihydroanthracen-9,10-imine and
2-isopropyl-9,10-diethyl-11-methyl-9,10-dihydroanthracen-9,10-imine Following the procedure described in Example 18, 1-isopropyl-9,10-diethyl-11-methyl-9,10-dihydroanthracen-9,10-imine and 2-isopropyl-9,10-diethyl-11-methyl-9,10-dihydroanthracen-9,10-imine are obtained from 1,3-diethyl-2-methylisoindole when the appropriate benzyne is generated in situ from the 2- and 4- chlorocumene, respectively. The chromatographically purified oily product, in each case, is dissolved in methanol and treated with a solution of maleic acid in methanol. Solvent is evaporated and the residue is partitioned between ether and water. The filtered aqueous solution is cooled, made strongly basic with aqueous sodium hydroxide and the oily base is extracted into benzene. Evaporation of the washed and dried extract under reduced pressure leaves the product as the residual yellow oil. The purified product, 1-isopropyl-9,10-diethyl-11-methyl-9,10-dihydroanthracen-9,10-imine, is obtained by short path distillation.

EXAMPLE 21

2-(N,N-Dimethylsulfamoyl)-9,10-diethyl-11-methyl-9,10-dihydroanthracen-9,10-imine Following the procedure described in Example 18, 2-(N,N-dimethylsulfamoyl)-9,10-diethyl-11-methyl-9,10-dihydroanthracen-9,10-imine is obtained from 1,3-diethyl-2-methylisoindole and the benzyne prepared in situ from 4-chloro-N,N-dimethylbenzenesulfonamide. The chromatographically purified (silica gel, 2% methanol/chloroform) oily product is triturated with a 2% aqueous solution of maleic acid. The filtered aqueous acid extract is cooled, made strongly basic with 40% sodium hydroxide, and the brown solid product collected.

The base is converted to the hydrogen oxalate salt by dissolving it in acetone saturated with oxalic acid. The salt precipitates and is recrystallized from methanol to obtain 2-(N,N-dimethylsulfamoyl)-9,10-diethyl-11-methyl-9,10-dihydroanthracen-9,10-imine hydrogen oxalate.

EXAMPLE 22

9,10-Diethyl-11-methyl-9,10-dihydroanthracen-9,10-imine-2-diethoxymethyl, and
9,10-diethyl-11-methyl-9,10-dihydroanthracen-9,10-imine-2-carboxaldehyde Following the procedure described in Example 18, the diethylacetal of 9,10-diethyl-11-methyl-9,10-dihydroanthracen-9,10-imine-2-carboxaldehyde is obtained from 1,3-diethyl-2-methylisoindole and the benzyne prepared in situ from the diethyl acetal of 4-chlorobenzaldehyde. The chromatographically purified (silica gel, 2% methanol/chloroform) oily product is dissolved in a solution of oxalic acid in acetone. Water is added and the solution heated to boiling to hydrolyze the acetal. Dilution with ether precipitates 9,10-diethyl-11-methyl-9,10-dihydroanthracen-9,10-imine-2-carboxaldehyde hydrogen oxalate hydrate which is recrystallized from acetone.

EXAMPLE 23

2-Cyano-9,10-diethyl-11-methyl-9,10-dihydroanthracen-9,10-imine

A solution of 0.00672 mole of 9,10-diethyl-11-methyl-9,10-dihydroanthracen-9,10-imine-2-carboxaldehyde hydrogen oxalate hydrate in 50 ml. of 95ethanol is treated with a solution of 0.6 g. (0.0084 mole) of hydroxylamine hydrochloride in 10 ml. of water followed by a solution of 0.8 g. (0.02 mole) of sodium hydroxide in 12 ml. of water. After 3 hours of stirring at room temperature, the mixture is poured into 300 ml. of ice and water and the pH adjusted to weakly basic with 5% aqueous sodium hydroxide. 9,10-Diethyl-11-methyl-9,10-dihydroanthracen-9,10-imine-2-carboxaldehyde oxime precipitates and is collected and dried.

A solution of 0.0065 mole of the oxime in 7 ml. of dry pyridine is stirred, cooled in ice, and treated dropwise with 1.6 g. (0.007 mole) of trifluoroacetic anhydride. After 20 hours at room temperature, the solution is evaporated under reduced pressure and the residue is partitioned between ether and water. The aqueous phase is separated, made weakly basic with 5% aqueous sodium hydroxide, and re-extracted with ether. The combined ether layers are washed with 10% aqueous sodium hydroxide and then with water. Evaporation of the dried extract under reduced pressure leaves 2-cyano-9,10-diethyl-11-methyl-9,10-dihydroanthracen-9,10-imine as a residual glass.

The base is converted to the hydrogen oxalate salt by dissolving it in acetone saturated with oxalic acid. The salt precipitates and is recrystallized twice from acetone to obtain 2-cyano-9,10-diethyl-11-methyl-9,10-dihydroanthracen-9,10-imine hydrogen oxalate.

EXAMPLE 24

2,3-Dimethylphthalimidine

A solution of 11.8 g. (0.076 mole) of 2-ethylbenzoic acid in 25 ml. of absolute methanol is treated cautiously with 2.5 ml. of concentrated sulfuric acid and heated to reflux. After 4 hours, the mixture is poured onto ice and the oily product is extracted into ether. Evaporation of the washed (water, 5% aqueous sodium bicarbonate and water) and dried extract under reduced pressure leaves methyl 2-ethylbenzoate as the residual colorless oil in a yield of 86%.

A mixture of 10.7 g. (0.065 mole) of methyl 2-ethylbenzoate, 12.5 g. (0.07 mole) of N-bromosuccinimide, 50 mg. of benzoyl peroxide, and 125 ml. of carbon tetrachloride is stirred at reflux until the reaction is complete in 2 hours. The precipitated succinimide is filtered from the cooled mixture and the filtrate is evaporated to dryness under reduced pressure leaving methyl 2-(1-bromoethyl)benzoate as the residual yellow oil in quantitative yield.

A solution of 0.156 mole of methyl 2-(1-bromomethyl)-benzoate and 24.0 g. (0.312 mole) of 40% aqueous methylamine in 230 ml. of absolute methanol is held at room temperature for 20 hours. Solvent is evaporated under reduced pressure and the residue partitioned between chloroform and water. Evaporation of the washed (water, 2N hydrochloric acid, and water) and dried chloroform extract under reduced pressure leaves the crude product as the residual oil. Distillation gives purified 2,3-dimethylphthalimidine as a fluid, colorless oil, b.p. 100°–110° C./0.2 mm. Hg. (84% yield).

EXAMPLE 25

2-Alkyl-3-methylphthalimidines

Following the procedure described in Example 24, methyl 2-(1-bromoethyl)benzoate is reacted with the appropriate primary amine to obtain the following 2-alkyl-3-methylphthalimidines:
1. 2-Benzyl-3-methylphthalimidine, b.p. 158°–162° C./0.1 mm. Hg.
2. 2-Ethyl-3-methylphthalimidine, b.p. 97°–105° C./0.1 mm. Hg.
3. 2-Cyclopropyl-3-methylphthalimidine, b.p. ca. 120° C./0.2 mm. Hg.
4. 2-(3-Hydroxypropyl)-3-methylphthalimidine, b.p. 172°–175° C./0.2 mm. Hg.
5. 2-Propyl-3-methylphthalimidine, b.p. 98°–104° C./0.1 mm. Hg.
6. 2-Butyl-3-methylphthalimidine, b.p. 109°–114° C./0.1 mm. Hg.
7. 2-Allyl-3-methylphthalimidine, b.p. 102°–104° C./0.15 mm. Hg.
8. 2-Cyclopropylmethyl-3-methylphthalimidine, b.p. 131°–133° C./0.1 mm. Hg.

EXAMPLE 26

1,2-Dimethyl-3-ethylisoindole

In a dry apparatus maintained in a nitrogen atmosphere, 45 ml. of 0.95 M ethyllithium in benzene is added dropwise to a stirred solution of 5.0 g. (0.031 mole) of 2,3-dimethylphthalimidine in 50 ml. of dry benzene. After stirring overnight at room temperature, the cooled mixture is hydrolyzed by the dropwise addition of 25 ml. of water. The benzene layer is separated and washed repeatedly with water. The combined aqueous layers are re-extracted with ether and the ether layer is washed repeatedly with water. The combined organic extracts are dried over anhydrous magnesium sulfate while stirring under nitrogen and cooling in an ice bath. Evaporation of the filtered solution under reduced pressure and drying of the residue at 0.1 mm. Hg. yields 1,2-dimethyl-3-ethylisoindole as a dark yellow oil.

EXAMPLE 27

2-Substituted-1-methyl-3-ethylisoindoles

Following the procedure described in Example 26, the appropriate 2-substituted-3-methylphthalimidine is treated with ethyllithium to obtain the following 2-alkyl-1-methyl-3-ethylisoindoles:
1. 2-Benzyl-1-methyl-3-ethylisoindole,
2. 2-Ethyl-1-methyl-3-ethylisoindole,
3. 2-Cyclopropyl-1-methyl-3-ethylisoindole,
4. 2-Propyl-1-methyl-3-ethylisoindole,
5. 2-Butyl-1-methyl-3-ethylisoindole,
6. 2-Allyl-1-methyl-3-ethylisoindole,
7. 2-[3-(Tetrahydropyranyl-2-oxy]propyl-1-methyl-3-ethylisoindole
8. 2-Cyclopropylmethyl-1-methyl-3-ethylisoindole,
9. 5-Chloro-; 5-iodo-; and 5-bromo-2-cyclopropyl-1-methyl-3-ethylisoindole,
10. 5-Chloro-; 5-iodo-; and 5-bromo-2-[3-(tetrahydropyranyl)-2-oxy]propyl-1-methyl-3-ethylisoindole,
11. 5-Chloro-; 5-iodo-; and 5-bromo-2-propyl-1-methyl-3-ethylisoindole.

EXAMPLE 28

2-[3-(Tetrahydropyranyl-2-oxy)-propyl]-3-methylphthalimidine

A mixture of 7.35 g. (0.036 mole) of 2-(3-hydroxypropyl)-3-methylphthalimidine, 3.3 g. (0.039 mole) of dihydropyran, 80 mg. of p-toluenesulfonic acid monhydrate and 75 ml. of absolute ether is stirred at room temperature for 24 hours. Stirring is continued for several hours after the addition of 1.0 g. of anhydrous potassium carbonate and the mixture is filtered. Evaporation of the filtrate under reduced pressure and drying of the residue at 0.5 mg. Hg. leaves 2-[3-(tetrahydropyranyl-2-oxy)-propyl]-3-methylphthalimidine as a viscous yellow oil in quantitative yield.

EXAMPLE 29

11-Benzyl-9-methyl-10-ethyl-9,10-dihydroanthracen-9,10-imine

Following the procedure described in Example 3, 11-benzyl-9,methyl-10-ethyl-9,10-dihydroanthracen-9,10-imine is obtained from 2-benzyl-1-methyl-3-ethylisoindole and benzyne generated in situ from 2-fluorobromobenzene. The crude, hexane-soluble, oily brown solid is purified by column chromatography on silica gel, the product being eluted with chloroform. Fractions containing a major component with a common $R_f$ value on a fluorescent silica thin layer plate developed with chloroform are combined. Evaporation of the solvent under reduced pressure leaves the product as a slightly oily, dark yellow solid. Two recrystallizations from absolute ethanol yield 11-benzyl-9-methyl-10-ethyl-9,10-dihydroanthracen-9,10-imine.

EXAMPLE 30

10-Ethyl-9,11-dimethyl-9,10-dihydroanthracen-9,10-imine

Following the procedure described in Example 3, 10-ethyl-9,11-dimethyl-9,10-dihydroanthracen-9,10-imine is obtained from 1-ethyl-2,3-dimethylisoindole and benzyne generated in situ from 2-fluorobromobenzene. The purified product is obtained by chromatography (silica gel, chloroform) as a red-brown oil (30% yield).

The base is converted to the fumaric acid salt by dissolving it and excess fumaric acid in absolute methanol. Dilution with ethyl acetate precipitates the salt which is recrystallized from methanol-ethyl acetate to obtain 10-ethyl-9,11-dimethyl-9,10-dihydroanthracen-9,10-imine fumaric acid salt as off-white crystals, m.p. 179°–180° C. dec.

Analysis Calc. for: $C_{18}H_{19}N.1.5C_4H_4O_4$: Calc.: C, 68.07; H, 5.95; N, 3.31. Found: C, 68.32; 68.11; H, 6.00; 6.31; N, 3.32; 3.16.

EXAMPLE 31

11-Cyclopropyl-9-methyl-10-ethyl-9,10-dihydroanthracen-9,10-imine

Following the procedure described in Example 3, 11-cyclopropyl-9-methyl-10-ethyl-9,10-dihydroanthracen-9,10-imine is obtained from 2-cyclopropyl-1-methyl-3-ethylisoindole and benzyne generated in situ from 2-fluorobromobenzene. The crude, hexane-soluble, oily yellow solid is sublimed to obtain the purified product.

The base is converted to the hydrogen oxalate salt by dissolving it in acetone saturated with oxalic acid.

Following the procedure described in Example 31, there is obtained:

2-chloro-11-cyclopropyl-9-methyl-10-ethyl-9,10-dihydroanthracen-9,10-imine;

2-iodo-11-cyclopropyl-9-methyl-10-ethyl-9,10-dihydroanthracen-9,10-imine;

2-bromo-11-cyclopropyl-9-methyl-10-ethyl-9,10-dihydroanthracen-9,10-imine; respectively, when the 2-cyclopropyl-1-methyl-3-ethyl-isoindole of Example 34 is replaced by an equivalent amount of 5-chloro-2-cyclopropyl-1-methyl-3-ethylisoindole;

5-iodo-2-cyclopropyl-1-methyl-3-ethylisoindole; and 5-bromo-2-cyclopropyl-1-methyl-3-ethylisoindole, respectively.

EXAMPLE 32

11-Benzyl-2,9-dimethyl-10-ethyl-9,10-dihydroanthracen-9,10-imine

Following the procedure described in Example 3, 11-benzyl-2,9-dimethyl-10-ethyl-9,10-dihydroanthracen-9,10-imine is obtained from 2-benzyl-1-methyl-3-ethylisoindole and the benzyne generated in situ from 3-bromo-4-chlorotoluene. The crude, hexane-soluble, dark oil is purified by gravity filtration of a benzene solution through a thick silica gel pad, washing the pad with benzene. Evaporation of the filtrate under reduced pressure leaves the product as the residual oily solid. Repeated recrystallizations from absolute ethanol give 11-benzyl-2,9-dimethyl-10-ethyl-9,10-dihydroanthracen-9,10-imine.

EXAMPLE 33

11-(3-Hydroxypropyl)-9-methyl-10ethyl-9,10-dihydroanthracen-9,10-imine

Following the procedure as described in Example 3, 11-[3-(tetrahydropyranyl-2-oxy)propyl]-9-methyl-10-ethyl-9,10-dihydroanthracan-9,10-imine is obtained from 2-[3-(tetrahydropyranyl-2-oxy)propyl]-1-methyl-3-ethylisoindole and benzyne generated in situ from 2-fluorobromobenzene. The crude, hexane-soluble, brown oil is hydrolyzed by stirring with 1.0 N hydrochloric acid for 4 hours at room temperature. The mixture is extracted with ether and the separated aqueous acid phase is cooled in ice and made strongly basic with 5% aqueous sodium hydroxide. The oily base is extracted into ether. Evaporation of the washed and dried extract under reduced pressure leaves the product as the residual dark oil. Purification is effected by gravity filtration of a chloroform solution through a thick silica gel pad, washing the pad with chloroform. Evaporation of the filtrate under reduced pressure leaves an oily brown solid that is recrystallized from petroleum ether to obtain 11-(3-hydroxypropyl)-9-methyl-10-ethyl-9,10-dihydroanthracen-9,10-imine.

Following the procedure described in Example 33, there is obtained:

2-chloro-11-(3-hydroxypropyl)-9-methyl-10-ethyl-9,10-dihydroanthracen-9,10-imine;

2-iodo-11-(3-hydroxypropyl)-9-methyl-10-ethyl-9,10-dihydroanthracen-9,10-imine; and 2-bromo-11-(3-hydroxypropyl)-9-methyl-10-ethyl-9,10-dihydroanthracen-9,10-imine, respectively, when the 2-[3-(tetrahydropyranyl-2-oxy)propyl]-1-methyl-3-ethylisoindole of Example 36 is replaced by an equivalent amount of 5-chloro-2-[3-(tetrahydropyranyl-2-oxy)propyl]-1-methyl-3-ethylisoindole;

5-iodo-2-[3-(tetrahydropyranyl-2-oxy)propyl]-1-methyl-3-ethylisoindole; and 5-bromo-2-[3-(tetrahydropyranyl-2-oxy)propyl]-1-methyl-3-ethylisoindole, respectively.

EXAMPLE 34

11-Propyl-9-methyl-10-ethyl-9,10-dihydroanthracen-9,10-imine

Following the procedure described in Example 3, 11-propyl-9-methyl-10-ethyl-9,10-dihydroanthracen-9,10-imine is obtained from 2-propyl-1-methyl-3-ethylisoindole and benzyne generated in situ from 2-fluorobromobenzene. The crude, hexane-soluble, dark oil is purified by gravity filtration of a benzene solution through a thick pad of silica gel, washing the pad with benzene-chloroform. Fractions of the filtrate containing a major basic component of common $R_f$ on a fluorescent silica thin layer plate developed with 1% methanol/chloroform are combined. Evaporation of the solvent under reduced pressure leaves the product as the residual oily solid.

The base is converted to the hydrogen oxalate salt by dissolving it in acetone saturated with oxalic acid. The salt precipitates and is recrystallized from acetone to obtain 11-propyl-9-methyl-10-ethyl-9,10-dihydroanthracen-9,10-imine hydrogen oxalate.

Following the procedure described in Example 34, there is obtained 2-chloro-11-propyl-9-methyl-10-ethyl-9,10-dihydroanthracen-9,10-imine;

2-iodo-11-propyl-9-methyl-10-ethyl-9,10-dihydroanthracen-9,10-imine; and 2-bromo-11-propyl-9-methyl-10-ethyl-9,10-dihydroanthracen-9,10-imine, respectively, when the 2-propyl-1-methyl-3-ethylisoindole of Example 34 is replaced by an equivalent amount of 5-chloro-2-propyl-1-methyl-3-ethylisoindole;

5-iodo-2-propyl-1-methyl-3-ethylisoindole; and 5-bromo-2-propyl-1-methyl-3-ethylisoindole, respectively.

EXAMPLE 35

11-Butyl-9-methyl-10-ethyl-9,10-dihydroanthracen-9,10-imine

Following the procedure described in Example 3, 11-butyl-9-methyl-10-ethyl-9,10-dihydroanthracen-9,10-imine is obtained from 2-butyl-1-methyl-3-ethylisoindole and benzyne generated in situ from 2-fluorobromobenzene. The crude, hexane-soluble, dark oil is purified by gravity filtration of a benzene solution through a thick pad of silica gel, washing the pad with benzene-chloroform. Fractions of the filtrate containing a major basic component of common $R_f$ on a fluorescent silica thin layer plate developed with chloroform are combined. Evaporation of the solvent under reduced pressure leaves the product as the residual oil.

The base is converted to the hydrogen oxalate salt by dissolving it in acetone saturated with oxalic acid. The salt precipitates and is recrystallized from acetone to obtain 11-butyl-9-methyl-10-ethyl-9,10-dihydroanthracen-9,10-imine hydrogen oxalate.

EXAMPLE 36

1-Chloro-9,11-dimethyl-10-ethyl-9,10-dihydroanthracen-9,10-imine

In a dry apparatus maintained in a nitrogen atmosphere, 0.95 g. (0.039 g. atom) of magnesium turnings are suspended in 10 ml. of dry tetrahydrofuran and the mixture is heated to refluxing. The reaction is initiated by the addition of a few drops of 2,6-dichlorobromobenzene and a mixture of 0.0337 mole of 1,2-dimethyl-3-ethylisoindole and 8.1 g. (0.036 mole) of 2,6-dichlorobromobenzene in 90 ml. of dry tetrahydrofuran is added dropwise. Stirring at reflux is continued for 16 hours when all of the magnesium is consumed. The cooled mixture is hydrolyzed by the dropwise addition of 20 ml. of water and the organic layer is decanted. Solvent is evaporated under reduced pressure and the residue is dissolved in ether-benzene. The filtered solution is washed with water, dried, and evaporated to dryness under reduced pressure, leaving the crude product as the residual oil. The oil is triturated with hexane and filtered from insoluble material. Evaporation of the hexane filtrate under reduced pressure leaves a dark oil that is chromatographed on silica gel. The product is eluted with benzene-chloroform and the fractions containing a major basic component of common $R_f$ on a fluorescent silica thin layer plate developed with 1% methanol/chloroform are combined. Evaporation of the solvent under reduced pressure leaves the product as the residual oil that is dissolved in acetone and treated with a solution of 4 g. of maleic acid in acetone. The solution is evaporated under reduced pressure and the residue is triturated repeatedly with water. The combined and filtered aqueous extracts are cooled in ice and made strongly basic with 40% aqueous sodium hydroxide. The oily base is extracted into ether. Evaporation of the washed and dried extract under reduced pressure leaves the product as the residual oily solid. Trituration with cold hexane and recrystallization from petroleum ether gives 1-chloro-9,11-dimethyl-10-ethyl-9,10-dihydroanthracen-9,10-imine.

The base is converted to the hydrogen oxalate salt by dissolving it in acetone saturated with oxalic acid containing a few drops of water. Dilution with absolute ether precipitates the salt and recrystallization from acetone gives 1-chloro-9,11-dimethyl-10-ethyl-9,10-dihydroanthracen-9,10-imine hydrogen oxalate.

EXAMPLE 37

11-Allyl-9-methyl-10-ethyl-9,10-dihydroanthracen-9,10-imine

Following the procedure described in Example 3, 11-allyl-9-methyl-10-ethyl-9,10-dihydroanthracen-9,10-imine is obtained from 2-allyl-1-methyl-3-ethylisoindole and benzyne generated in situ from 2-fluorobromobenzene. The chromatographically purified (silica gel, benzene-chloroform) oil product crystallizes from cold petroleum ether. Two recrystallizations from petroleum ether, using decolorizing charcoal, give 11-allyl-9-methyl-10-ethyl-9,10-dihydroanthracen-9,10-imine.

The base is converted to the hydrogen oxalate salt by dissolving it in acetone saturated with oxalic acid.

EXAMPLE 38

11-Cyclopropylmethyl-9-methyl-10-ethyl-9,10-dihydroanthracen-9,10-imine

Following the procedure described in Example 3, 11-cyclopropylmethyl-9-methyl-10-ethyl-9,10-dihydoranthracen-9,10-imine is obtained from 2-cyclopropylmethyl-1-methyl-3-ethylisoindole and benzyne generated in situ from 2-fluorobromobenzene. The chromatographically purified (silica gel, benzene-chloroform) oily product crystallizes on trituration with petroleum ether.

The base is converted to the hydrogen oxalate salt by dissolving it in acetone saturated with oxalic acid. The salt precipitates and is recrystallized from acetone to obtain 11-cyclopropylmethyl-9-methyl-10-ethyl-9,10-dihydroanthracen-9,10-imine hydrogen oxalate.

EXAMPLE 39

11-(3-Dimethylaminopropyl)-9-methyl-10-ethyl-9,10-dihydroanthracen-9,10-imine To a stirred mixture of 1.45 g. (0.0052 mole) of 11-(3-hydroxypropyl)-9-methyl-10-ethyl-9,10-dihydroanthracen-9,10-imine, 1.4 g. (0.00525 mole) of triphenylphosphine, and 17 ml. of dry benzene at room temperature and under nitrogen is added, in portions, 0.95 g. (0.00535 mole) of N-bromosuccinimide. Stirring is continued for 6 hours as a fine white precipitate slowly separates. After cooling in an ice-bath, the mixture is saturated with gaseous dimethylamine and stirring is continued overnight at room temperature. Solvent is evaporated under reduced pressure and the residue is triturated with absolute ether. The precipitate of succinimide is filtered and the filtrate is evaporated to dryness under reduced pressure. The residue is triturated with hot hexane and this mixture is chilled. After filtration of the precipitate of triphenylphosphine oxide, the hexane filtrate is evaporated to dryness under reduced pressure leaving the product as the residual oil which is purified by short path distillation.

The base is converted to the hydrochloride salt by treating an ethanolic solution with an equivalent of hydrogen chloride in ethanol. Dilution with absolute ether precipitates the salt which is recrystallized from cold absolute ethanol-ether to obtain 11-(3-dimethylaminopropyl)-9-methyl-10-ethyl-9,10-dihydroanthracen-9,10-imine hydrochloride.

Following the procedure described in Example 39 except that the 11-(3-hydroxypropyl)-9-methyl-10-ethyl-9,10-dihydroanthracen-9,10-imine of Example 39 is replaced by equivalent amount of 2-chloro-11-(3-hydroxypropyl)-9-methyl-10-dihydroanthracen-9,10-imine;
2-iodo-11(3-hydroxypropyl)-9-methyl-10-ethyl-9,10-dihydroanthracen-9,10-imine; and
2-bromo-11-(3-hydroxypropyl)-9-methyl-10-ethyl-9,10-dihydroanthracen-9,10-imine; respectively, there is obtained 2-chloro-11-(3-dimethylaminopropyl)-9-methyl-10-ethyl-9,10-dihydroanthracen-9,10-imine;
2-iodo-11-(3-dimethylaminopropyl)-9-methyl-10-ethyl-9,10-dihydroanthracen-9,10-imine; and
2-bromo-11-(3-dimethylaminopropyl)-9-methyl-10-ethyl-9,10-dihydroanthracen-9,10-imine, respectively.

EXAMPLE 40

9-Methyl-10-ethyl-9,10-dihydroanthracen-9,10-imine

A solution of 0.0074 mole of 11-benzyl-9-methyl-10-ethyl-9,10-dihydroanthracen-9,10-imine in 25 ml. of glacial acetic acid is stirred with 200 mg. of 5% palladium/carbon under hydrogen at atmospheric pressure until the absorption of hydrogen is complete. The catalyst is removed by filtration and evaporation of the filtrate under reduced pressure leaves the crude product as the residual oily solid. A solution of the residue is benzene-ether (1:1) is extracted with 0.5 M. citric acid. The aqueous acidic extract is cooled and made strongly basic with 40% aqueous sodium hydroxide. The oily base is extracted into benzene-ether (1:1). Evaporation of the washed and dried organic extract under reduced pressure leaves the product as oily white crystals which are purified by sublimation.

EXAMPLE 41

1-Vinyl-2,3-dimethylisoindole

In a dry apparatus maintained in a nitrogen atmosphere, 17 ml. of 2.5 M. vinyllithium in tetrahydrofuran is added dropwise to a stirred solution of 5.0 g. (0.031 mole) of 2,3-dimethylphthalimidine in 50 ml. of dry tetrahydrofuran. After stirring 3 days at room temperature, the mixture is hydrolyzed by the dropwise addition of 4 ml. of water and filtered, washing the precipitate with ether. The filtrate is dried over anhydrous magnesium sulfate while stirring under nitrogen. Evaporation of the filtered solution under reduced pressure and drying of the residue at 0.5 mm. yields 1-vinyl-2,3-dimethylisoindole.

EXAMPLE 42

10-Vinyl-9,11-dimethyl-9,10-dihydroanthracen-9,10-imine

Following the procedure described in Example 3,10-vinyl-9,11-dimethyl-9,10-dihydroanthracen-9,10-imine is obtained from 1-vinyl-2,3-dimethylisoindole and benzyne generated in situ from 2-fluorobromobenzene. The purified product is obtained by column chromatography (silica gel, chloroform) as a brown oil.

The base is converted to the fumaric acid salt by dissolving it and excess fumaric acid in absolute methanol. Dilution with ethyl acetate precipitates the salt which is recrystallized from methanol-ethyl acetate, yielding the fumaric acid salt of 10-vinyl-9,11-dimethyl-9,10-dihydroanthracen-9,10-imine as off-white crystals, m.p. 154°–156° C. dec.

Analysis calc. for: $C_{18}H_{17}N \cdot 1.5 C_4H_4O_4$: Calc.: C, 68.40; H, 5.50; N, 3.32, Found: C, 68.30; H, 5.72; N, 3.19.

EXAMPLE 43

N-Carboethoxy-9-methyl-10-ethyl-9,10-dihydroanthracen-9,10-imine

A solution of 0.1 mole of 9-methyl-10-ethyl-9,10-dihydroanthracen-9,10-imine in 150 ml. of chloroform is treated with 10.1 g. (0.1 mole) of triethylamine and cooled to 0° C. with stirring. To this stirred solution is added dropwise a solution of 12.7 g. (0.11 mole) of ethyl chloroformate in 25 ml. of $HCCl_3$. Stirring is continued for 2 hours at room temperrature. The reaction mixture is poured into 300 ml. of ice water. The organic phase is separated and washed with ice water, 5% aqueous hydrochloric acid, 5% aqueous sodium bicarbonate and then with water. The organic solution is dried over $Na_2SO_4$, filtered and the filtrate evaporated to yield N-carboethoxy-9-methyl-10-ethyl-9,10-dihydroanthracen-9,10-imine.

EXAMPLE 44

N-Carboethoxy-2-nitro-9-methyl-10-ethyl-9,10-dihydroanthracen-9,10-imine

A solution of 0.05 mole of N-carboethoxy-9-methyl-10-ethyl-9,10-dihydroanthracen-9,10-imine in 25 ml. of tetramethylenesulfone is added dropwise to a stirred slurry of 7.3 g. (0.05 mole) of nitronium tetrafluoroborate in 50 ml. of tetramethylenesulfone at 15° C. Stirring at 30° C. is continued for an additional two hours. The reaction mixture is poured into 300 grams of ice water and the product collected by filtration to yield N-carboethoxy-2-nitro-9-methyl-10-ethyl-9,10-dihydroanthracen-9,10-imine.

EXAMPLE 45

N-Carboethoxy-2-amino-9-methyl-10-ethyl-9,10-dihydroanthracen-9,10-imine

A solution of N-carboethoxy-2-nitro-9-methyl-10-ethyl-9,10-dihydroanthracen-9,10-imine (16.9 g., .05 mole) in 100 ml. of ethanol is hydrogenated over 5% Pd/C (1.0 g.) at room temperature and atmospheric pressure for 2 hours. The catalyst is separated by filtration and the solvent is evaporated to yield N-carboethoxy-2-amino-9-methyl-10-ethyl-9,10-dihydroanthracen-9,10-imine.

EXAMPLE 46

N-Carboethoxy-2-hydroxy-9-methyl-10-ethyl-9,10-dihydroanthracen-9,10-imine

A stirred slurry of 9.8 g. (.032 moles) of N-carboethoxy-2-amino-9-methyl-10-ethyl-9,10-dihydroanthracen-9,10-imine in 150 ml. of ice water containing 6.4 ml. of concentrated sulfuric acid is treated dropwise with a solution of 2.34 g. of sodium nitrite in 20 ml. of water at 0° C. The resulting solution of the diazonium salt is added to a solution of 6.4 g. of concentrated sulfuric acid in 200 ml. of $H_2O$ preheated to 80° C. The resulting reaction mixture is maintained at this temperature for 20 minutes. The reaction mixture is cooled to 0° C. and the product N-carboethoxy-2-hydroxy-9-methyl-10-ethyl-9,10-dihydroanthracen-9,10-imine is collected by filtration.

EXAMPLE 47

N-Carboethoxy-2-methoxy-9-methyl-10-ethyl-9,10-dihydroanthracen-9,10-imine

A solution of 4.9 g. (.016 mole) of N-carboethoxy-2-hydroxy-9-methyl-10-ethyl-9,10-dihydroanthracen-9,10-imine in 100 ml. of methanol is treated 5.0 g. of diazomethane in ether. The resulting solution is allowed to stand at room temperature overnight. Evaporation of solvent gives N-carboethoxy-2-methoxy-9-methyl-10-ethyl-9,10-dihydroanthracen-9,10-imine.

EXAMPLE 48

9,11-Dimethyl-10-ethyl-2-methoxy-9,10-dihydroanthracen-9,10-imine

A solution of 2.5 g. (.008 mole) of N-carboethoxy-2-methoxy-9-methyl-10-ethyl-9,10-dihydroanthracen-9,10-imine in 50 ml. of ether is added dropwise to a stirred slurry of 2.0 g. of lithium aluminum hydride in 100 ml. of ether. The slurry is stirred and heated under reflux for 8 hours. Water is added cautiously and the inorganic material is separated by filtration. Evaporation of the filtrate gives 9,11-dimethyl-10-ethyl-2-methoxy-9,10-dihydroanthracen-9,10-imine.

EXAMPLE 49

2-Bromo-9,10-diethyl-11-methyl-9,10-dihydroanthracen-9,10-imine

A mixture of .01 mole of 9,10-diethyl-11-methyl-9,10-dihydroanthracen-9,10-imine and 0.03 mole of thallium (III) acetate in 100 ml. of carbon tetrachloride under nitrogen is stirred rapidly as a solution of 0.01 mole of bromine in 50 ml. of carbon tetrachloride is added dropwise. The mixture is heated under reflux for 30 minutes. The cooled reaction mixture is filtered and then washed with aqueous sodium metalbisulfite, aqueous sodium bicarbonate and water. The solvent is evaporated and the residue taken up in chloroform and filtered down a short column of alumina to yield 2-bromo-9,10-diethyl-11-methyl-9,10-dihydroanthracen-9,10-imine.

EXAMPLE 50

2-Nitro-9,10-diethyl-11-methyl-9,10-dihydroanthracen-9,10-imine

A solution of 0.1 mole of 9,10-diethyl-11-methyl-9,10-dihydroanthracen-9,10-imine in 25 ml. of tetramethylenesulfone is added dropwise to a stirred slurry of 14.6 g. (0.1 mole) of nitronium tetrafluoroborate in 70 ml. of tetramethylene sulfone at 15° C. Stirring at room temperature is continud an additional two hours. The reaction mixture is poured into 350 grams of ice water and then neutralized with aqueous ammonia. The product is separated by filtration and dissolved in isopropyl alcohol saturated with fumaric acid; on cooling 2-nitro-9,10-diethyl-11-methyl-9,10-dihydroanthracen-9,10-imine hydrogen fumarate is obtained and purified by recrystallization from isopropanol.

EXAMPLE 51

2-Amino-9,10-diethyl-11-methyl-9,10-dihydroanthracen-9,10-imine

A solution of 2-iodo-9,10-diethyl-11-methyl-9,10-dihydroanthracen-9,10-imine (0.02 mole) and bistrimethylsilylamidocopper prepared in situ from hexamethyldisilazine, n-butyllithium and copper (I) iodide in 100 ml. of dry pyridine is heated under reflux for 20 hours. The solvent is evaporated and 100 ml. of methanol added. The methanol slurry is stirred at 35° C. for 2 hours and then the solvent is evaporated. The reaction mixture is extracted with dilute aqueous fumaric acid. The acid extract is made basic with aqueous ammonia and then extracted with ether. The ether extract is dried over anhydrous sodium sulfate, filtered, and the filtrate evaporated to yield 2-amino-9,10-diethyl-11-methyl-9,10-dihydroanthracen-9,10-imine.

EXAMPLE 52

9-Methyl-10,11-diethyl-9,10-dihydroanthracen-9,10-imine

A solution of 0.01 mole of 9-methyl-10-ethyl-9,10-dihydroanthracen-9,10-imine and 1.56 g. (0.01 mole) of ethyl iodide in 100 ml. of acetonitrile is slurried with 2.0 g. of sodium bicarbonate and heated at 45° C. for 6 hours. The solvent is evaporated. The residue is distributed between 5% aqueous ammonium hydroxide and ether. The ether solution is separated, dried over sodium sulfate, filtered and the filtrate evaporated to yield 9-methyl-10,11-diethyl-9,10-dihydroanthracen-9,10-imine.

EXAMPLE 53

9-Methyl-10-ethyl-11-propyl-9,10-dihydroanthracen-9,10-imine

To a solution of .01 mole of 9-methyl-10-ethyl-9,10-dihydroanthracen-9,10-imine and 1.06 g. (.02 mole) of propionaldehyde in 45 ml. of acetonitrile is added 2.5 g. of sodium cyanoborohydride. The pH of the reaction mixture is adjusted to pH 7.0 with aqueous acetic acid and the reaction mixture is stirred overnight. The solvent is evaporated. Aqueous potassium hydroxide is added and the aqueous mixture is extracted with ether. The ether extract is dried over sodium sulfate, filtered and evaporated to yield 9-methyl-10-ethyl-11-propyl-9,10-dihydroanthracen-9,10-imine.

EXAMPLE 54

N-Carboethoxy-2-acetyl-9-methyl-10-ethyl-9,10-dihydroantracen-9,10-imine

To a solution of methyl oxocarbonium hexafluoroantimonate (13.9 g., .05 mole) in 50 ml. of nitromethane is added 14.6 g. (0.05 mole) of N-carboethoxy-9-methyl-10-ethyl-9,10-dihydroanthracen-9,10-imine. The reaction mixture is stirred for 3 hours at 45° C. and then poured into water. The aqueous mixture is extracted with ether. The ether extract is washed several times with water and then dried over sodium sulfate, filtered and the filtrate evaporated to yield N-carboethoxy-2-acetyl-9-methyl-10-ethyl-9,10-dihydroanthracen-9,10-imine.

EXAMPLE 55

Preparation of 3,9,11-trimethyl-9,10-dihydroanthracen-9,10-imine sesqui hydrogen fumarate Step A.: 2,5-Dimethylphthalimidine A mixture of 4-methylphthallic anhydride (48.63 g., 0.30 mole), methylamine hydrochloride (40.5 g., 0.60 mole), sodium acetate (49.23 g., 0.60 mole) and acetic acid (1000 ml.) is heated to reflux for two hours. The hot mixture is filtered and the filtrate cooled to 75°. Zinc dust (95 g.) is added rapidly with stirring and the mixture heated to reflux for an additional four hours. The hot mixture is filtered and the filtrate is evaporated to a small volume under reduced pressure. Saturated sodium bicarbonate solution (600 ml.) is added gradually with stirring and the resulting solution is extracted with chloroform (4 × 200 ml.). The chloroform extracts are washed with sodium bicarbonate solution (100 ml.), water (100 ml.), saturated NaCl solution (250 ml.) and dried (magnesium sulfate). Removal of the solvent under reduced pressure leaves a waxy solid, 25.1 g., m.p. 38-47° C.

Step B: 1,2,5-Trimethylisoindole

A solution of methyllithium in ether (55 ml., 1.8 M) is added dropwise to a stirred solution of 2,5-dimethylphthalimidine (11.9 g., 0.074 mole) in ether (200 ml.) under nitrogen. The mixture is stirred for 5 hours, water (100 ml.) is added dropwise, and the layers are separated. The ether layer is washed with saturated NaCl solution and dried (potassium carbonate). The solvent is removed under reduced pressure and the residual oil is dried under vacuum (0.1 mm. Hg.) protected from light, 9.3 g.

Step C.:
3,9,11-Trimethyl-9,10-dihydroanthracen-9,10-imine sesqui hydrogen fumarate A portion of a solution of 2-bromofluorobenzene (12.25 g., 0.070 mole) in tetrahydrofuran (50 ml.) is added to a stirred mixture of magnesium turnings (1.68 g., 0.070 mole), 1,2,5-trimethylisoindole (9.2 g., 0.60 mole) and tetrahydrofuran (50 ml.) under nitrogen. The Grignard reaction is initiated and the remainder of the bromofluorobenzene solution is added dropwise. Upon complete addition the mixture is heated under reflux for 3 hours and the solvent is removed under reduced pressure. The residue is dissolved in benzene (250 ml.), washed with saturated ammonium chloride solution (2 × 100 ml.), water (3 × 100 ml.), saturated sodium chloride solution (150 ml.) and dried (sodium sulfate). The solvent is removed under reduced pressure and the residue is extracted with hexane. The oil which is obtained upon evaporation of the hexane extracts is treated with oxalic acid as described for 2,9,11-trimethylanthracen-9,10-imine, and the resulting oil is purified by chromatography over silica gel eluting with chloroform. The pure base from the chromatography (1.1 g.), is dissolved in ethyl acetate (15 ml.) and added to a hot solution of fumaric acid in 2-propanol (15 ml.). The solid that forms is collected (1.1 g.) and recrystallized from ethyl acetate to give 3,9,11-trimethyl-9,10-dihydroanthracen-9,10-imine sesqui hydrogen fumarate, 0.80 g., m.p. 125°-127° C.

Analysis calc. for: $C_{17}H_{17}N - 1.5C_4H_4O_4$: Calc: C, 67.46; H, 5.66; N, 3.42, Found: C, 67.34; H, 5.89; N, 3.47.

EXAMPLE 56

Preparation of 2,9,11-trimethyl-9,10-dihydroanthracen9,10-imine sesqui hydrogen fumarate STEP A.: 6-methylphthalimidine A mixture of m-toluic acid (27.2 g., 0.20 mole), N-hydroxyphthalimide (35.44 g., 0.20 mole), and concentrated sulfuric acid (200 ml.) is heated on the steam bath with stirring for twenty-four hours. The cooled solution is poured onto crushed ice and the material that separates is collected, washed with benzene, followed by 5% sodium hydroxide solution and dried, 12.85 g. Recrystallization from benzene gives 6-methylphthalimidine, 10.0 g., m.p. 204-206°.

STEP B.: 2,6-Dimethylphthalimidine

Sodium hydride (5.0 g., 57% oil dispersion) is added to a stirred solution of 6-methylphthalimidine (14.5 g.,) and methyl iodide (40 g.,) in DMF (400 ml.) under nitrogen. After an initial vigorous reaction the mixture is kept at ambient temperature for twenty-four hours. The solvent is removed under reduced pressure and the residue dissolved in water (400 ml.). The aqueous solution is extracted with chloroform and the chloroform is evaporated. The residual oil is dissolved in ether, dried over anhydrous magnesium sulfate and the ether is evaporated. The residue is dissolved in ethyl acetate (50 ml.) and diluted gradually with hexane (200 ml.). The solid that forms is collected and dried, (6.3 g., m.p. 85-88°.

STEP C.: 1,2,6-Trimethylisoindole

A solution of methyl lithium in ether (50 ml., 1.8 M) is added dropwise to a stirred solution of 2,6-dimethylphthalimidine (9.45 g.) in ether (200 ml.) under nitrogen. After 5 hours, water (150 ml.) is added and the layers are separated. The ether layer is washed with saturated salt solution and dried over anhydrous potassium carbonate. The solvent is evaporated under reduced pressure and the resulting yellow-orange powder is dried in vacuum (0.05 mm. Hg.) protected from light, 8.6 g.

STEP D.:
2,9,11-Trimethyl-9,10-dihydroanthracen9,10-imine sesqui hydrogen fumarate A portion of a solution of 2-bromofluorobenzene (10.3 g., 0.059 mole) in tetrahydrofuran (50 ml.) is added to a mixture of magnesium turnings (1.6 g., 0.066 g-at.), 1,2,6-trimethylisoindole (8.6 g., 0.054 mole) and tetrahydrofuran (50 ml.) under nitrogen. The Grignard reaction is intiated and the remainder of the bromofluorobenzene solution is added dropwise. Upon complete addition the mixture is heated under reflux for 5 hours and the solvent is removed under reduced pressure. The residue is partitioned between ether (250 ml.) and saturated ammonium chloride solution (100 ml.). The ether layer is washed with saturated ammonium chloride solution (100 ml.), water (100 ml.), and saturated NaCl solution (100 ml.) and dried over anhydrous potassium carbonate. The solvent is removed under reduced pressure and the residual oil is extracted with hexane (400 ml.). The hexane is evaporated under reduced pressure, and the residual oil (8.6 g.) is dissolved in the minimum volume of 2-propanol and mixed with a solution of oxalic acid (3.3. g.) in 2-propanol (75 ml.). The solvent is evaporated and the residue is dissolved in water (250 ml.). After extraction of the aqueous solution with ether, it is made alkaline by the addition of 20% sodium hydroxide solution. The alkaline solution is extracted with ether (300 ml.), the ether washed with water, saturated sodium chloride and dried (potassium carbonate). The oil obtained on evaporation of the solvent (4.4. g.) is dissolved in ethyl acetate (50 ml.) and added to a boiling solution of 2-propanol (50 ml.). Removal of the solvent under reduced pressure and addition of acetone to the residue produced 3.3 g. of off-white solid, m.p. 132°-135° C. Recrystallization from acetone gives 2,9,11-trimethyl-9,10-dihydroanthracen9,10-imine sesqui hydrogen fumarate, m.p. 131°-136° C.

Analysis calc. for: $C_{17}H_{17}N + 1.5C_4H_4O_4$: Calc.: C, 67.46; H, 5.66; N, 3.42. Found: C, 67.53; H, 5.78; N, 3.36.

EXAMPLE 57

Preparation of 9,11-dimethyl-9,10-dihydroanthracen-9,10-imine hydrogen oxalate

STEP A.: 1,2-Dimethylisoindole

A solution of methyl lithium in ether (53 ml., 1.9M) is added dropwsie to a stirred suspension of N-methylphthalimidine (14.7 g., 0.1 mole) in ether (200 ml.) under nitrogen. After complete addition the mixture is stirred for four hours, followed by dropwise addition of water (150 ml.). The layers are separated and the aqueous phase extracted with ether (100 ml.). The combined organic extracts are washed with saturated sodium chloride solution and dried over anhydrous potassium carbonate. The solvent is removed under reduced pressure and the residue is dried under vacuum (0.1 mm) in the absence of light to yield a yellow-orange oil, 12.5 g.

STEP B.:
9,11-Dimethyl-9,10-dihydroanthracen9,10-imine hydrogen oxalate

A portion of a solution of 2-bromofluorobenzene (13 g.) in tetrahydrofuran (50 ml.) is added to a mixture of magnesium turnings (2.0 g.), 1,2-dimethylisoindole (12.5 g.) and tetrahydrofuran (50 ml.) under nitrogen. The Grignard reaction is initiated and the remainder of the bromofluorobenzene solution is added dropwise. Upon complete addition, the mixture is refluxed for two hours, cooled, and poured into saturated ammonium chloride solution (150 ml.). The layers are separated and the aqueous phase extracted with tetrahydrofuran (300 ml.). The organic extracts are combined and dried over anhydrous potassium carbonate. The solvent is removed and the residual dark oil (20.9 g.) is dissolved in 2-propanol (250 ml.). A solution of oxalic acid (9.0 g., 0.1 mole) in 2-propanol (250 ml.) is added, followed by ethyl acetate (500 ml.) and the solution is cooled. Filtration and drying gives 4.38 g. of blue powder, m.p. 134°-136° C. Recrystallization from acetone utilizing Darco gives 2.32 g. of 9,10-dimethyl9,10-dihydroanthracen-9,10-imine hydrogen oxalate as a white solid, m.p. 139-140° C.

Analysis calc. for: $C_{16}H_{15}N+C_2H_2O_4$: Calc.: C, 69.44; H, 5.50; N, 4.50. Found: C, 69.50; H, 5.72; N, 4.58.

EXAMPLE 58

Preparation of 2-chloro-9,11-dimethyl-9,10dihydroanthracen9,10imine hydrogen fumarate STEP A.: 6-Chlorophthalimidine N-Hydroxymethylphthalimide (8.86 g., 0.050 mole) is added to a stirred solution of m-chlorobenzoic acid (7.83 g., 0.050 mole) in concentrated sulfuric acid (250 ml.). The solution is warmed on the steam bath for 18 hours, cooled and poured over ice (1500 g.). The solid that separates is collected, washed with water and dried, 8.0 g., m.p. 130°-220° C. Recrystallization from 2-propanol gives material with m.p. 254°-256.5° C., 6chlorophthalimidine.

Analysis calc. for: $C_8H_6ClNO$:
Calc.: C, 57.33; H, 3.61; N, 8.36. Found: C, 56.68; H, 3.56; N, 8.06.

STEP B.: 6-chloro-2-methylphthalimidine

To a stirred mixture of sodium hydride (4.3 g., 57% oil dispersion, 0.1 mole) and benzene (100 ml.) is added a slurry of 6-chlorophthalimidine (16.75 g., 0.10 mole) in DMF (250 ml.). When gas evolution diminishes the mixture is warmed on the steam bath for two hours and cooled. Methyl iodide (21.3 g., 0.15 mole) in benzene (100 ml.) is added dropwise. After stirring for eighteen hours the mixture is filtered and the filtrate evaporated under reduced ressure. The residue is mixed with water, filtered and dried, 10.52 g. Recrystallization from carbon tetrachloride-hexane gives 6-chloro-2-methylphthalimidine, m.p. 95°-98° C.

STEP C.: 6-chloro-1,2-dimethylisoindole

A solution of methyl lithium in ether (35 ml., 1.8M) is added dropwise to a stirred suspension of 6-chloro-2-methylphthalimidine (8.75 g., 0.048 mole) in ether (150 ml.) under nitrogen. After complete addition, the mixture is stirred for 5 hours and water (50 ml.) is added dropwise. The layers are separated and the ether layer is washed with saturated salt solution and dried over anhydrous postassium carbonate. The solvent is removed under reduced pressure and the dark reddish solid is dried under vacuum protected from light, 6.2 g.

STEP D.:
2-Chloro-9,11-dimethyl-9,10-dihydroanthracen-9,10-imine hydrogen fumarate A portion of a solution of 2-bromofluorobenzene (6.5 g., 0.037 mole) in tetrahydrofuran (25 ml.) is added to a mixture of magnesium turnings (0.89 g., 0.037 mole), 6-chloro-1,2-dimethylisoindole (6.2 g., 0.035 mole) and tetrahydrofuran (25 ml.) under nitrogen. The Grignard reaction is initiated and the remainder of the bromofluorobenzene solution is added dropwise. Upon complete addition, the mixture is refluxed for five hours and the solvent is removed under reduced pressure. The residue is dissolved in ether-benzene (200 ml.) and mixed with saturated ammonium chloride solution. The organic layer is separated, washed with water and saturated NaCl solution, and dried over anhydrous potassium carbonate. The solvent is removed under reduced pressure and the residue (5.19 g., red oil) is mixed with oxalic acid (2.5 g.) in ethanol (25 ml.). Ethanol is removed under vacuum and the residue is dissolved in water (125 ml.). The aqueous solution is extracted with ether then made alkaline by the addition of 20% sodium hydroxide solution. The basic solution is extracted with ether, these extracts washed with water, saturated NaCl solution, and dried over anhydrous potassium carbonate. The solvent is removed and the residue is treated with oxalic acid as previously described. The resulting light yellow oil (1.9 g.) is dissolved in ethyl acetate (30 ml.) and added to a hot solution of fumaric acid (1.3 g.) in 2-propanol (25 ml.). The solid that forms on cooling is collected and dried, 2.0 g., m.p. 154-156° C., 2-chloro-9,11-dimethyl-9,10-dimethyl-9,10-dihydroanthracen-9,10-imine hydrogen fumarate.

Analysis calc. for: $C_{16}H_{14}ClN+C_4H_4O_4$:, Calc.: C, 64.60; H, 4.88; N, 3.77; Cl, 9.54., Found: C, 64.84; H, 5.18; N, 3.73; Cl, 9.34.

EXAMPLE 59

Preparation of 9-ethyl-11-methyl-9,10-dihydroanthracen-9,10-imine sesqui hydrogen fumarate Step A.: 1-Ethyl-2-methylisoindole A solution of ethyl lithium (110 ml., 0.95M) in benzene is added to a suspension of N-methylphthalimidine (14.7 g., 0.10 mole) in ether (200 ml.) under nitrogen. The mixture is stirred for twenty-four hours, water (100 ml.) is added dropwise, and the layers are separated. The ether layer is washed with saturated sodium chloride solution (100 ml.) and dried (potassium carbonate). Evaporation of the solvent under reduced pressure and drying of the residual oil at 0.3 mm in the absence of light yields 15.05 g.

Step B.:
9-Ethyl-11-methyl-9,10-dihydroanthracen-9,10-imine sesqui hydrogen fumarate A portion of a solution of 2-bromofluorobenzene (17.5 g., 0.10 mole) in tetrahydrofuran (75 ml.) is added to a mixture of magnesium turnings (2.4 g., 0.10 mole), 1-ethyl-2-methylisoindole (15 g., 0.094 mole) and tetrahydrofuran (75 ml.) under nitrogen. The Grignard reaction is initiated and the remainder of the bromofluorobenzene solution is added dropwise. Upon complete addition the mixture is heated to reflux for two hours followed by twenty hours at 25° C. The solvent is removed under reduced pressure and the residue is partitioned between benzene (200 ml.) and saturated ammonium chloride solution (150 ml.). After separation and drying (potassium carbonate) the solvent is removed under reduced pressure to yield a dark oil. After extraction with hexane and treatment with oxalic acid, as described for 2,9,11-trimethyl-9,10-dihydroanthracen-9,10-imine, a dark oil (8.15 g.) is obtained. A solution of this oil in ethyl acetate (75 ml.) is added to a boiling solution of fumaric acid (4.02 g.) in 2-propanol (75 ml.). The resulting solid is collected (5.25 g.) and recrystallized from acetone to give 9-ethyl-11-methyl-9,10-dihydroanthracen-9,10-imine, 2.34 g.

Analysis calc. for: $C_{17}H_{17}N = 1.5C_4H_4O_4$: Calc.: C, 67.47; H, 5.66; N, 3.42. Found: C, 67.87; H,5.81; N, 3.39.

EXAMPLE 60

Preparation of
11-benzyl-9-methyl-9,10-dihydroanthracen-9,10-imine sesqui hydrogen fumarate Step A.: 2-Benzyl-1-methylisoindole A solution of methyl lithium in ether (50 ml., 1.8M) is added dropwise to a stirred solution of N-benzylphthalimidine (13.1 g, 0.059 mole) in ether (400 ml.) under nitrogen. The mixture is kept for six hours, water (100 ml.) is added dropwise, and the layers are separated. The aqueous layer is extracted with ether (100 ml.) and the combined ether solutions are washed with saturated NaCl solution (400 ml.) and dried (potassium carbonated). The solvent is removed under reduced pressure and the residual oil is dried under vacuum (0.1 mm. Hg.) protected from light, 12.8 g.

Step B.:
11-Benzyl-9-methyl-9,10-dihydranthracen-9,10-imine sesqui hydrogen fumarate A portion of a solution of 2-bromofluorobenzene (12.25 g., 0.070 mole) in tetrahydrofuran (50 ml.) is added to a stirred mixture of magnesium turnings (1.68 g., 0.070 mole), 2-benzyl-1-methylisoindole (12.7 g., 0.058 mole) and tetrahydrofuran (50 ml.) under nitrogen. The Grignard reaction is initiated and the remainder of the bromofluorobenzene solution is added dropwise. Upon complete addition the mixture is heated to reflux for four hours and the solvent is removed under reduced pressure. The residue is dissolved in benzene (250 ml.) and washed with saturated ammonium chloride solution (2 × 100 ml.), water (3 × 100 ml.), saturated salt solution (2 × 150 ml.), and dried (sodium sulfate). The solvent is removed and the residual oil is extracted with hexane and treated with oxalic acid as described for 2,9,11-trimethyl-9,10-dihydroanthracen-9,10-imine. The oil (3.87 g.) from this treatment is dissolved in ethyl acetate (40 ml.) and is added to a hot solution of fumaric acid (2.26 g.) in 2-propanol (40 ml.). The solid that separates (3.3 g., m.p. 119°-122° C.) is collected and recrystallized from ethyl acetate-2-propanol to give 11-benzyl-9-methyl-9,10-dihydroanthracen-9,10-imine sesqui hydrogen fumarate, sinters 110-114° C., decomposes with effervescence 192°-195° C.

Analysis calc. for: $C_{22}H_{19}N + 1.5C_4H_4O_4$: Calc.: C, 71.32; H, 5.34; N, 2.97. Found: C, 71.18; H, 5.40; N, 2.85

EXAMPLE 61

Preparation of
11-ethyl-9-methyl-9,10-dihydroanthracen-9,10-imine hydrogen fumarate Step A.: 2-Ethyl-1-methylisoindole A solution of methyl lithium in ether (60 ml., 1.8M) is added dropwise to a stirred solution of 2-ethylphthalimidine (16.1 g., 0.10 mole) in ether (300 ml.) under nitrogen. The mixture is stirred for eighteen hours, water (200 ml.) is added dropwise, and the layers, are separated. The ether layer is washed with saturated salt solution and dried (potassium carbonate). The solvent is removed under reduced pressue and the residual oil is dried under vacuum (0.1 mm. Hg.) protected from light, 15.1 g.

Step B.:
11-Ethyl-9-methyl-9,10-dihydroanthracen-9,10-imine hydrogen fumarate

A portion of a solution of 2-bromofluorobenzene (17.5 g., 0.10 mole) in tetrahydrofuran (75 ml.) is added to a stirred mixture of magnesium turnings (2.4 g., 0.10 mole), 2-ethyl-1methylisoindole (15. 1 g.) and tetrahydrofuran (75 ml.) under nitrogen. The Grignard reaction is initiated and the remainder of the bromofluorobenzene solution is added dropwise. Upon complete addition the mixture is heated to reflux for twenty hours and the solvent is removed under reduced pressure. The residue is partitioned between benzene (200 ml.) and saturated ammonium chloride (200 ml.). After separation the benzene layer is washed with water (300 ml.), saturated NaCl solution (100 ml.) and dried (potassium carbonate). The solvent is removed under reduced pressue and the residue is extracted with hexane (300 ml.). The hexane is evaporated and the oily residue is treated with oxalic acid (4.5 g.), as described for 2,9,11-trimethyl-9,10-dihydroanthracen-9,10imine. The oil (5.8 g.) obtained from this treatment is dissolved in ethyl acetate (100 ml.) and is added to a hot solution of fumaric acid in 2-propanol (100 ml.). The solid that separates on cooling (4.9 g.) is collected and recrystallized from acetone to give 11-ethyl-9methyl-9,10-dihydroanthracen-9,10-imine hydrogen fumarate, 3.9 g., m.p. 132-134° (turns to glass, Liquifies gradually over 150°).

Analysis calc. for: $C_{17}H_{17}N + C_4H_4O_4$: Calc.: C, 71.78; H, 6.02; N, 3.99. Found: C, 71.39; H, 6.21; N, 3.94.

EXAMPLE 62

Preparation of intravenous solutions

A solution containing 10 mg. of 9,10-diethyl-11-methyl-9,10-dihydroanthracen-9,10-imine per ml. of injectable solution is prepared in the following manner.

A mixture of 10 mg. of 9,10-diethyl-11-methyl-9,10-dihydroanthracen-9,10-imine and 9 mg. of sodium chloride is dissolved in sufficient water for injection to make 1 ml. of solution. The pH is adjusted using hydrochloric acid or aqueous sodium hydroxide to about pH 7.0.

If it is desired that the intravenous solution be used for multi-dose purposes, 1.0 mg. of methyl-p-hydroxybenzoate (methyl paraben) and 0.10 mg. of n-propyl-p-hydroxy benzoate (propyl paraben) are mixed with the other solids before adding water to dissolve the solids.

The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.1, 1.0, 100.0 mg., respectively, of 9,10-diethyl-11-methyl-9,10-dihydroanthracen-9,10-imine per ml. of soltuion are similarly prepared substituting the indicated amount for the above-illustrated 10 mg. quantity. Bulk injectable solutions of convenient volume for subsequent delivery in unit dosage form are readily prepared following the above procedure.

Following the above procedure, other representative injectable solutions of the present invention are prepared when the 9,10-diethyl-11-methyl-9,10-dihydroanthracen-9,10-imine is replaced by an equivalent amount of 2-fluoro-9,10-diethyl-11-methyl-9,10-dihydroanthracen-9,10-imine or by an equivalent amount of any of the anthracenimine of the present invention.

EXAMPLE 63

Tablet Preparation

Tablets containing 1.0, 2.0, 25.0, 26.0, 50.0, and 100.0 mg., respectively, of 9,10-diethyl-11-methyl-9,10-dihydroanthracen-9,10-imine are prepared as illustrated below.

| TABLE FOR DOSES CONTAINING FROM 1-25 MG. OF THE ANTHRACENIMINE COMPOUND | | | |
|---|---|---|---|
| | Amount - mg | | |
| 9,10-diethyl-11-methyl-9,10-dihydroanthracen-9,10-imine | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26-100 MG. OF THE ANTHRACENIMINE COMPOUND | | | |
|---|---|---|---|
| | Amount - mg. | | |
| 9,10-diethyl-11-methyl-9,10-dihydroanthracen-9,10-imine | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | .39 | 0.75 | 1.5 |

All of the 9,10-diethyl-11-methyl-9,10-dihydroanthracen-9,10-imine, lactose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg., 2.0 mg., 25.0 mg., 26.0 mg., 50.0 mg., and 100.0 mg. of 9,10-diethyl-11-methyl-9,10-dihydroanthracen-9,10-imine per tablet.

Following the above procedure, tablets comprising 2-fluoro-9,10-diethyl-11-methyl-9,10-dihydroanthracen-9,10-imine are prepared when the 9,10-diethyl-11-methyl-9,10-dihydroanthracen-9,10-imine is replaced by an equivalent amount of 2-fluoro-9,10-diethyl-11-methyl-9,10-dihydroanthracen-9,10-imine. Other tablets are prepared using the same procedures and the equivalent amounts of excipients along with equivalent amounts of the anthracenimine compounds of the present invention.

What is claimed is:

1. A compound selected from the group consisting of:

2-bromo-11-methyl-9,10-dihydroanthracen-9,10-imine;
2-methoxy-11-methyl-9,10-dihydroanthracen-9,10-imine;
9,10-diethyl-11-methyl-9,10-dihydroanthracen-9,10-imine;
2-chloro-11-propyl-9,10-diethyl-9,10-dihydroanthracen-9,10-imine;
2-iodo-11-propyl-9,10-diethyl-9,10-dihydroanthracen-9,10-imine;
2-bromo-11-propyl-9,10-diethyl-9,10-dihydroanthracen-9,10-imine;
2-chloro-11-cyclopropyl-9,10-diethyl-9,10-dihydroanthracen-9,10-imine;
2-iodo-11-cyclopropyl-9,10-diethyl-9,10-dihydroanthracen-9,10-imine;
2-bromo-11-cyclopropyl-9,10-diethyl-9,10-dihydroanthracen-9,10-imine;
2-chloro-11-(3-hydroxypropyl)-9,10-diethyl-9,10-dihydroanthracen-9,10-imine;
2-iodo-11-(3-hydroxypropyl)-9,10-diethyl-9,10-dihydroanthracen-9,10-imine;
2-bromo-11-(3-hydroxypropyl)-9,10-diethyl-9,10-dihydroanthracen-9,10-imine;
9,10-dihydro-2,11-dimethyl-9,10-diethylanthracen-9,10-imine;
2-chloro-9,10-dihydro-9,10-diethyl-11-methylanthracen-9,10-imine;
9,10-dihydro-1-fluoro-9,10-diethyl-11-methylanthracen-9,10-imine;
9,10-dihydro-2-methoxy-9,10-diethyl-11-methylanthracen-9,10-imine;
9,10-dihydro-9,10-diethyl-1,11-dimethylanthracen-9,10-imine;
9,10-dihydro-2-trifluoromethyl-9,10-diethyl-11-methylanthracen-9,10-imine;
9,10-dihydro-2-fluoro-9,10-diethyl-11-methylanthracen-9,10-imine;
2-bromo-9,10-dihydro-9,10-diethyl-11-methylanthracen-9,10-imine;
2-cyano-9,10-dihydro-9,10-diethyl-11-methylanthracen-9,10-imine;
2-methylthio-9,10-diethyl-11-methyl-9,10-dihydroanthracen-9,10-imine;
1-isopropyl-9,10-diethyl-11-methyl-9,10-dihydroanthracen-9,10-imine;
2-isopropyl-9,10-diethyl-11-methyl-9,10-dihydroanthracen-9,10-imine;
2-(N,N-dimethylsulfamoyl)-9,10-diethyl-11-methyl-9,10-dihydroanthracen-9,10-imine;
2-diethoxymethyl-9,10-diethyl-11-methyl-9,10-dihydroanthracen-9,10-imine;
11-benzyl-9-methyl-10-ethyl-9,10-dihydroanthracen-9,10-imine;
10-ethyl-9,11-dimethyl-9,10-dihydroanthracen-9,10-imine;
11-benzyl-2,9-dimethyl-10-ethyl-9,10-dihydroanthracen-9,10-imine;
11-(3-hydroxypropyl)-9-methyl-10-ethyl-9,10-dihydroanthracen-9,10-imine;
11-propyl-9-methyl-10-ethyl-9,10-dihydroanthracen-9,10-imine;
11-butyl-9-methyl-10-ethyl-9,10-dihydroanthracen-9,10-imine;
1-chloro-9,11-dimethyl-10-ethyl-9,10-dihydroanthracen-9,10-imine;
11-allyl-9-methyl-10-ethyl-9,10-dihydroanthracen-9,10-imine;

11-cyclopropylmethyl-9-methyl-10-ethyl-9,10-dihydroanthracen-9,10-imine;
11-(3-dimethylaminopropyl)-9-methyl-10-ethyl-9,10-dihydroanthracen-9,10-imine;
2-iodo-11-(3-dimethylaminopropyl)-9-methyl-10-ethyl-9,10-dihydroanthracen-9,10-imine;
2-bromo-11-(3-dimethylaminopropyl)-9-methyl-10-ethyl-9,10-dihydroanthracen-9,10-imine;
9-methyl-10-ethyl-9,10-dihydroanthracen-9,10-imine;
10-vinyl-9,11-dimethyl-9,10-dihydroanthracen-9,10-imine;
2-methoxy-9,11-dimethyl-10-ethyl-9,10-dihydroanthracen-9,10-imine;
2-bromo-9,10-diethyl-11-methyl-9,10-dihydroanthracen-9,10-imine;
2-nitro-9,10-diethyl-11-methyl-9,10-dihydroanthracen-9,10-imine;
2-amino-9,10-diethyl-11-methyl-9,10-dihydroanthracen-9,10-imine;
3,9,11-trimethyl-9,10-dihydroanthracen-9,10-imine;
2,9,11-trimethyl-9,10-dihydroanthracen-9,10-imine;
2-chloro-9,11-dimethyl-9,10-dihydroanthracen-9,10-imine;
9,11-dimethyl-9,10-dihydroanthracen-9,10-imine;
9,11-dimethyl-10-ethyl-9,10-dihydroanthracen-9,10-imine;
9,10-bis(trifluoromethyl)-11-methyl-9,10-dihydroanthracen-9,10-imine;
11-methyl-9,10-dipropyl-9,10-dihydroanthracen-9,10-imine;
11-methyl-9-ethyl-10-propyl-9,10-dihydroanthracen-9,10-imine;
2-carboxaldehyde-9,10-diethyl-11-methyl-9,10-dihydroanthracen-9,10-imine; and
9,10,11-triethyl-9,10-dihydroanthracen-9,10-imine.

2. 2-Bromo-11-methyl-9,10-dihydroanthracen-9,10-imine according to claim 1.
3. 2-Methoxy-11-methyl-9,10-dihydroanthracen-9,10-imine according to claim 1.
4. 9,10-Diethyl-11-methyl-9,10-dihydroanthracen-9,10-imine according to claim 1.
5. 2-Chloro-11-propyl-9,10-diethyl-9,10-dihydroanthracen-9,10-imine according to claim 1.
6. 2-Iodo-11-propyl-9,10-diethyl-9,10-dihydroanthracen-9,10-imine according to claim 1.
7. 2-Bromo-11-propyl-9,10-diethyl-9,10-dihydroanthracen-9,10-imine according to claim 1.
8. 2-Chloro-11-cyclopropyl-9,10-diethyl-9,10-dihydroanthracen-9,10-imine according to claim 1.
9. 2-Iodo-11-cyclopropyl-9,10-diethyl-9,10-dihydroanthracen-9,10-imine according to claim 1.
10. 2-Bromo-11-cyclopropyl-9,10-diethyl-9,10-dihydroanthracen-9,10-imine according to claim 1.
11. 2-Chloro-11-(3-hydroxypropyl)-9,10-diethyl-9,10-dihydroanthracen-9,10-imine according to claim 1.
12. 2-Iodo-11-(3-hydroxypropyl)-9,10-diethyl-9,10-dihydroanthracen-9,10-imine according to claim 1.
13. 2-Bromo-11-(3-hydroxypropyl)-9,10-diethyl-9,10-dihydroanthracen-9,10-imine according to claim 1.
14. 9,10-Dihydro-2,11-dimethyl-9,10-diethyl-anthracen-9,10-imine according to claim 1.
15. 2-Chloro-9,10-dihydro-9,10-diethyl-11-methylanthracen-9,10-imine according to claim 1.
16. 9,10-Dihydro-1-fluoro-9,10-diethyl-11-methylanthracen-9,10-imine according to claim 1.
17. 9,10-Dihydro-2-methoxy-9,10-diethyl-11-methylanthracen-9,10-imine according to claim 1.
18. 9,10-Dihydro-9,10-diethyl-1,11-dimethyl-anthracen-9,10-imine according to claim 1.
19. 9,10-dihydro-2-trifluoromethyl-9,10-diethyl-11-methylanthracen-9,10-imine according to claim 1.
20. 9,10-Dihydro-2-fluoro-9,10-diethyl-11-methylanthracen-9,10-imine according to claim 1.
21. 2-Bromo-9,10-dihydro-9,10-diethyl-11-methylanthracen-9,10-imine according to claim 1.
22. 2-Cyano-9,10-dihydro-9,10-diethyl-11-methyl-anthracen-9,10-imine according to claim 1.
23. 2-Methylthio-9,10-diethyl-11-methyl-9,10-dihydroanthracen-9,10-imine according to claim 1.
24. 1-Isopropyl-9,10-diethyl-11-methyl-9,10-dihydroanthracen-9,10-imine according to claim 1.
25. 2-Isopropyl-9,10-diethyl-11-methyl-9,10-dihydroanthracen-9,10-imine according to claim 1.
26. 2-(N,N-Dimethylsulfamoyl)-9,10-diethyl-11-methyl-9,10-dihydroanthracen-9,10-imine according to claim 1.
27. 2-Diethoxymethyl-9,10-diethyl-11-methyl-9,10-dihydroanthracen-9,10-imine according to claim 1.
28. 11-Benzyl-9-methyl-10-ethyl-9,10-dihydroanthracen-9,10-imine according to claim 1.
29. 10-Ethyl-9,11-dimethyl-9,10-dihydroanthracen-9,10-imine according to claim 1.
30. 11-Benzyl-2,9-dimethyl-10-ethyl-9,10-dihydroanthracen-9,10-imine according to claim 1.
31. 11-(3-Hydroxypropyl)-9-methyl-10-ethyl-9,10-dihydroanthracen-9,10-imine according to claim 1.
32. 11-Propyl-9-methyl-10-ethyl-9,10-dihydroanthracen-9,10-imine according to claim 1.
33. 11-Butyl-9-methyl-10-ethyl-9,10-dihydroanthracen-9,10-imine according to claim 1.
34. 1-Chloro-9,11-dimethyl-10-ethyl-9,10-dihydroanthracen-9,10-imine according to claim 1.
35. 11-Allyl-9-methyl-10-ethyl-9,10-dihydroanthracen-9,10-imine according to claim 1.
36. 11-Cyclopropylmethyl-9-methyl-10-ethyl-9,10-dihydroanthracen-9,10-imine according to claim 1.
37. 11-(3-Dimethylaminopropyl)-9-methyl-10-ethyl-9,10-dihydroanthracen-9,10-imine according to claim 1.
38. 2-Iodo-11-(3-dimethylaminopropyl)-9-methyl-10-ethyl-9,10-dihydroanthracen-9,10-imine according to claim 1.
39. 2-Bromo-11-(3-dimethylaminopropyl)-9-methyl-10-ethyl-9,10-dihydroanthracen-9,10-imine according to claim 1.
40. 9-Methyl-10-ethyl-9,10-dihydroanthracen-9,10-imine according to claim 1.
41. 10-Vinyl-9,11-dimethyl-9,10-dihydroanthracen-9,10-imine according to claim 1.
42. 2-Methoxy-9,11-dimethyl-10-ethyl-9,10-dihydroanthracen-9,10-imine according to claim 1.
43. 2-Bromo-9,10-diethyl-11-methyl-9,10-dihydroanthracen-9,10-imine according to claim 1.
44. 2-Nitro-9,10-diethyl-11-methyl-9,10-dihydroanthracen-9,10-imine according to claim 1.
45. 2-Amino-9,10-diethyl-11-methyl-9,10-dihydroanthracen-9,10-imine according to claim 1.
46. 3,9,11-Trimethyl-9,10-dihydroanthracen-9,10-imine according to claim 1.
47. 2,9,11-Trimethyl-9,10-dihydroanthracen-9,10-imine according to claim 1.
48. 2-Chloro-9,11-dimethyl-9,10-dihydroanthracen-9,10-imine according to claim 1.
49. 9,11-Dimethyl-9,10-dihydroanthracen-9,10-imine according to claim 1.

50. 9,11-Dimethyl-10-ethyl-9,10-dihydroanthracen-9,10-imine according to claim 1.

51. 9,10-Bis(trifluoromethyl)-11-methyl-9,10-dihydroanthracen-9,10-imine according to claim 1.

52. 11-Methyl-9,10-dipropyl-9,10-dihydroanthracen-9,10-imine according to claim 1.

53. 11-Methyl-9-ethyl-10-propyl-9,10-dihydroanthracen-9,10-imine according to claim 1.

54. 2-Carboxaldehyde-9,10-diethyl-11-methyl-9,10-dihydroanthracen-9,10-imine according to claim 1.

55. 9,10,11-Triethyl-9,10-dihydroanthracen-9,10-imine according to claim 1.

* * * * *